(12) United States Patent
Bachovchin

(10) Patent No.: US 9,839,646 B2
(45) Date of Patent: *Dec. 12, 2017

(54) SMALL MOLECULE ENHANCER FOR DENDRITIC CELL CANCER VACCINES

(71) Applicant: Trustees of Tufts College, Boston, MA (US)

(72) Inventor: William W. Bachovchin, Cambridge, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,777

(22) Filed: Nov. 23, 2015

(65) Prior Publication Data
US 2016/0310513 A1    Oct. 27, 2016

Related U.S. Application Data

(63) Continuation of application No. 14/353,408, filed as application No. PCT/US2012/065236 on Nov. 15, 2012, now Pat. No. 9,284,337.

(60) Provisional application No. 61/562,497, filed on Nov. 22, 2011.

(51) Int. Cl.
| | | |
|---|---|---|
| A61K 31/40 | (2006.01) | |
| A61K 31/69 | (2006.01) | |
| C07F 5/02 | (2006.01) | |
| A61K 35/17 | (2015.01) | |
| A61K 39/00 | (2006.01) | |
| A61N 5/10 | (2006.01) | |
| A61K 38/05 | (2006.01) | |
| A61K 38/20 | (2006.01) | |
| A61K 38/21 | (2006.01) | |
| A61K 45/06 | (2006.01) | |

(52) U.S. Cl.
CPC .............. *A61K 31/69* (2013.01); *A61K 35/17* (2013.01); *A61K 38/05* (2013.01); *A61K 38/20* (2013.01); *A61K 38/21* (2013.01); *A61K 39/0005* (2013.01); *A61K 39/0011* (2013.01); *A61K 45/06* (2013.01); *A61N 5/10* (2013.01); *C07F 5/025* (2013.01); *A61K 2039/5154* (2013.01); *A61K 2039/5158* (2013.01)

(58) Field of Classification Search
USPC ........................................................ 514/408
See application file for complete search history.

(56) References Cited

U.S. PATENT DOCUMENTS

| 6,040,145 A * | 3/2000 | Huber ..................... A61K 38/55 424/94.64 |
| 7,799,782 B2 | 9/2010 | Munson et al. |
| 7,998,997 B2 | 8/2011 | Bachovchin et al. |
| 8,268,880 B2 | 9/2012 | Bachovchin et al. |
| 9,284,337 B2 * | 3/2016 | Bachovchin ............ C07F 5/025 |
| 2009/0124559 A1 | 5/2009 | Bachovchin et al. |
| 2010/0105753 A1 | 4/2010 | Bachovchin et al. |

FOREIGN PATENT DOCUMENTS

| WO | WO-2000/010549 A1 | 3/2000 |
| WO | WO-2000/071135 | 11/2000 |
| WO | WO-2007/123686 A2 | 11/2007 |

OTHER PUBLICATIONS

Adams, S. et al., "PT-100, a Small Molecule Dipeptidy Peptidase Inhibitor, Has Potent Antitumor Effects and Augments Antibody-Mediated Cytotoxicity via a Novel Immune Mechanism", *Cancer Research*, 64(15):5471-5480 (American Cancer Society, USA, Aug. 2004).
Coutts, S. J. et al., "Structure-Activity Relationships of Boronic Acid Inhibitors of Dipeptidyl Peptidase IV. 1. Variation of the $P_2$ Position of $X_{aa}$-boroPro Dipeptides", *Journal of Medicinal Chemistry*, 39(10):2087-2094 (American Chemical Society, USA, Jan. 1996).
Extended European Search Report from parent PCT application PCT/US2012/065236 dated Jun. 11, 2015.
International Search Report and Written Opinion from parent PCT application PCT/US2012/065236 dated Mar. 27, 2013.
Nemunaitis, J. et al., "Phase I Trial of PT-100 (PT-100), A Cytokine-Inducing Small Molecule, Following Chemotherapy for Solid Tumor Malignancy", *Cancer Investigation*, 24(6):553-561 (US, Sep. 2006).
Pennisi, A. et al., "Inhibitor of DASH proteases affects expression of adhesion molecules in osteoclasts and reduces myeloma growth and bone disease", *British Journal of Hematology*, 145(6):775-787 (Blackwell Publishing Ltd., UK, Jun. 2009).
Thuy Tran, et al., "Synthesis and Structure-Activity Relationship of N-Acyl-Gly-, N-Acl-Sar- and N-Blocked-Boropro Inhibitors of FAP, TPP4, and POP," Bioorg Med Chem Lett, 17(5): 1438-1442.
Zhang, J. et al., "Potential anti-tumor effect of a small molecule dipeptidyl peptidase inhibitor, 4175, in colorectal cancer", Abstract 5226, *Cancer Research*, 72(8) (American Association of Cancer Research, USA, Apr. 15, 2012).

* cited by examiner

*Primary Examiner* — Rei Tsang Shiao
(74) *Attorney, Agent, or Firm* — Foley Hoag LLP

(57) ABSTRACT

Disclosed is a method of treating cancer, comprising administering to a mammal in need thereof a therapeutically effective amount of a compound that inhibits a plurality of mammalian DASH serine proteases. Also disclosed is a method of (a) increasing antitumor immunity, (b) stimulating or enhancing an immune response, (c) treating a condition characterized by abnormal cell proliferation, (d) increasing cytokine and/or chemokine production, or (e) stimulating or enhancing production of T-cells, in a mammal, comprising administering to a mammal in need thereof an effective amount of a compound that inhibits a plurality of mammalian DASH serine proteases. For example, the compound that inhibits a plurality of mammalian DASH serine proteases may be t-butylGly-boroPro.

16 Claims, 25 Drawing Sheets

Val-boroPro

Ala-boroPro

| | \multicolumn{8}{c|}{$K_i / IC_{50}*$ (nM)} | | | | | | | |
|---|---|---|---|---|---|---|---|---|
| | DPPIV | DPP8 | DPP9 | DPPII | FAP | PREP | MTD (mg/kg) | Immune Stimulation |
| V-bP | 0.18 | 1.5 | 0.76 | 8.2* | 17* | 35* | 0.05 | G-CSF, IL-1β, INFγ |
| A-bP | 0.027 | 2.0 | 0.53 | 1.4* | 43* | 240* | >200 | No |

| | \multicolumn{5}{c|}{In Vitro $IC_{50}$ (nM)} | | | | |
|---|---|---|---|---|---|
| Compound | DPPIV | DPP8 | DPP9 | DPPII | FAP |
| PT-100 | 0.7 | 3.6 | 1.7 | 8.2 | 17 |
| ARI-4175 | 1.6 | 5.1 | 1.9 | 88 | 32 |

MTD study in SD Rats
Plasma taken 30 min Post-Dose

- SQ Val-boroPro
- SQ Tle-boroPro
- Oral Val-boroPro
- Oral Tle-boroPro

Survival (number surviving/total per group) listed for each experiment.

| Drug Concentration (nM) | | | | |
|---|---|---|---|---|
| Dose (mg/kg) | Val-bPro (SQ) | Tle-bPro (SQ) | Val-bPro (PO) | Tle-bPro (PO) |
| 0.01 | 13.67 (0.64) | 11.11 (0.19) | | |
| 0.025 | 58.58 (2.25) | 58.83 (1.41) | | |
| 0.05 | 150.54 (8.49) | 107.80 (8.41) | 0.45 (0.58) | 11.90 (1.82) |
| 0.1 | | | 166.44 (11.41) | 51.37 (5.30) |
| 0.25 | | | | 154.74 (19.76) |

Standard Error in Parentheses.

SMALL MOLECULE ENHANCER FOR DENDRITIC CELL CANCER VACCINES

RELATED APPLICATIONS

This application is a continuation of U.S. patent application Ser. No. 14/353,408 filed Apr. 22, 2014; which is the U.S. national phase of International Patent Application No. PCT/US2012/065236, filed Nov. 15, 2012; which claims the benefit of priority to U.S. Provisional Patent Application Ser. No. 61/562,497, filed Nov. 22, 2011.

BACKGROUND OF THE INVENTION

Cancer is America's second leading cause of death. Approved anticancer agents, both chemotherapeutic and targeted agents, are limited by toxicity and are ultimately ineffective against solid tumors, e.g.: lung, colorectal, breast, pancreatic, and prostate cancers, which account for more than 85% of cancer deaths. To kill tumors using the body's immune system, the failure of which has allowed the cancer to emerge, has long been the goal of cancer research. Val-boroPro, also known as PT-100 or talabostat, is a dipeptide boronic acid that showed remarkable efficacy in shrinking tumors in mice through immune activation. However, in Fast Track Phase III clinical trials, it did not meet its objectives, due to dose-limiting toxicity.

The US Food and Drug Administration approved the first cancer vaccine, Provenge for prostate cancer, on Apr. 29, 2010. Provenge is a dendritic cell therapy (DCT); one of several exciting new immunotherapies sometimes called "cancer vaccines". By supercharging the immune system, such vaccines can, in principle, find and remove the very last cancer cell, no matter where it hides, thus precluding mere remission after a course of treatment. Although the concept is now proven, cancer vaccines, including DCTs other than Provenge, have failed to achieve the desired efficacy in clinical trials, indicating the need to add immune stimulators, or adjuvants. However, less toxic adjuvants are needed to develop this approach clinically.

SUMMARY OF THE INVENTION

One aspect of the present invention relates to a method of treating cancer, comprising administering to a mammal in need thereof a therapeutically effective amount of a compound that inhibits a plurality of mammalian DASH serine proteases.

Another aspect of the invention relates to a method of increasing antitumor immunity in a mammal, comprising administering to a mammal in need thereof an effective amount of a compound that inhibits a plurality of mammalian DASH serine proteases.

Another aspect of the invention relates to a method of stimulating or enhancing an immune response in a mammal, comprising administering to a mammal in need of an effective amount of a compound that inhibits a plurality of mammalian DASH serine proteases.

Yet another aspect of the invention relates to a method of treating a condition characterized by abnormal cell proliferation, comprising administering to a mammal in need thereof a therapeutically effective amount of a compound that inhibits a plurality of mammalian DASH serine proteases.

Another aspect of the invention relates to a method of increasing cytokine and chemokine production in a mammal, comprising administering to a mammal in need thereof an effective amount of a compound that inhibits a plurality of mammalian DASH serine proteases.

Another aspect of the invention relates to a method of stimulating or enhancing production of T-cells in a mammal, comprising administering to a mammal in need thereof an effective amount of a compound that inhibits a plurality of mammalian DASH serine proteases, wherein said T cells recognize an antigen on a malignant cell.

In certain embodiments, the invention relates to any one of the methods described above, wherein the compound is represented by Formula I:

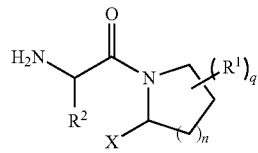

Formula I wherein:

X is $B(Y^1)(Y^2)$ or CN;

$Y^1$ and $Y^2$ are independently OH, or together with the boron atom to which they are attached represent a group that is hydrolysable to a boronic acid, or together with the boron atom to which they are attached form a 5- to 8-membered ring that is hydrolysable to a boronic acid;

$R^1$ is selected from the group consisting of halogen, lower alkyl, lower alkenyl, lower alkynyl, carbonyl, carboxyl, ester, formate, ketone, thiocarbonyl, thioester, thioacetate, thioformate, amino, acylamino, amido, nitro, sulfate, sulfonate, sulfonamido, $-(CH_2)_m-R_7$, $-(CH_2)_m-OH$, $-(CH_2)_m-O$-lower alkyl, $-(CH_2)_m-O$-lower alkenyl, $-(CH_2)_n-O-(CH_2)_m-R_7$, $-(CH_2)_m-SH$, $-(CH_2)_m-$S-lower alkyl, $-(CH_2)_m-$S-lower alkenyl, or $-(CH_2)_n-$S$-(CH_2)_m-R_7$, azido, cyano, isocyanato, thiocyanato, isothiocyanato, cyanato,

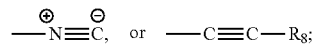

$R_7$ represents a substituted or unsubstituted aryl, aralkyl, cycloalkyl, cycloalkenyl, or heterocycle;

$R_8$ independently represents hydrogen, $-CH_3$, or $-(CH_2)_n-CH_3$;

m is 0, 1, 2, 3, 4, 5, or 6;

$R^2$ is a hydrophobic group selected from the group consisting of n-propyl, $C_4$-$C_8$ alkyl, $C_2$-$C_8$alkenyl, $C_2$-$C_8$alkynyl, $C_3$-$C_8$cycloalkyl, $C_2$-$C_7$heterocyclyl, aryl, heteroaryl, aralkyl, heteroaralkyl, and side chains of naturally occurring hydrophobic amino acids;

n is 0, 1, or 2; and q is 0, 1, 2, 3, or 4.

In certain embodiments, the invention relates to any one of the methods described above, wherein the compound is t-butylGly-boroPro.

BRIEF DESCRIPTION OF THE DRAWINGS

FIG. 8 B shows that ARI-4175 increases mouse survival in a rhabdomyosarcoma (RMS) model. C57BL/6 mice were injected intramuscularly with RMS cells on day 0. Mice received a single subcutaneous vaccination on day 10 followed by daily gavage of 10 mg/kg (5 days) and 5 mg/kg (10 days) ARI-4175, 1 mg/kg PT-100 (15 days), or vehicle as described in Example 1.

FIG. 13 B shows the in vivo inhibition by ARI-4175 of colon cancer xenografts. The figure shows the inhibition of HCT-116 by ARI-4175 alone or in combination with cetuximab (CTX).

FIG. 17 B shows that as adjuvant to tumor-primed T cell transfer, ARI-4175 induces tumor regression in late treatment RMS M3-9-M model.

FIG. 18 B shows that combination treatment with ARI-4175 and adoptive T cell transfer in Rag1−/− recipients significantly reduces RMS M3-9-M volume: by day 10, ARI-4175 treated mice had significantly smaller tumors than saline treated mice (naïve: n=5, p=0.0159; primed: n=5, p=0.0079).

Rag1$^{-/-}$ mice treated with tumor-primed T cells in combination with ARI-4175 had the smallest tumors overall.

Figure 19:
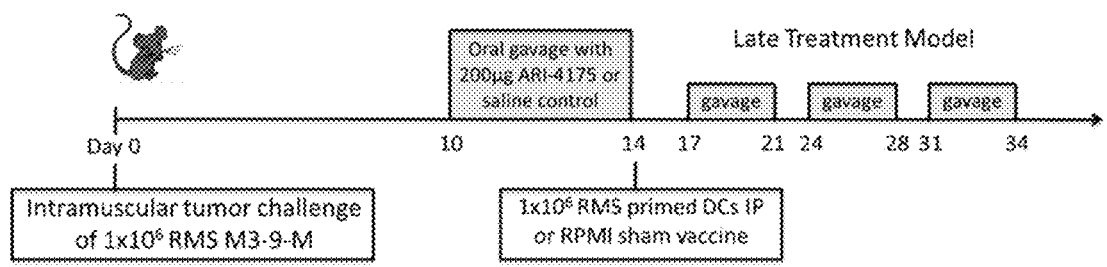
Figure 19:
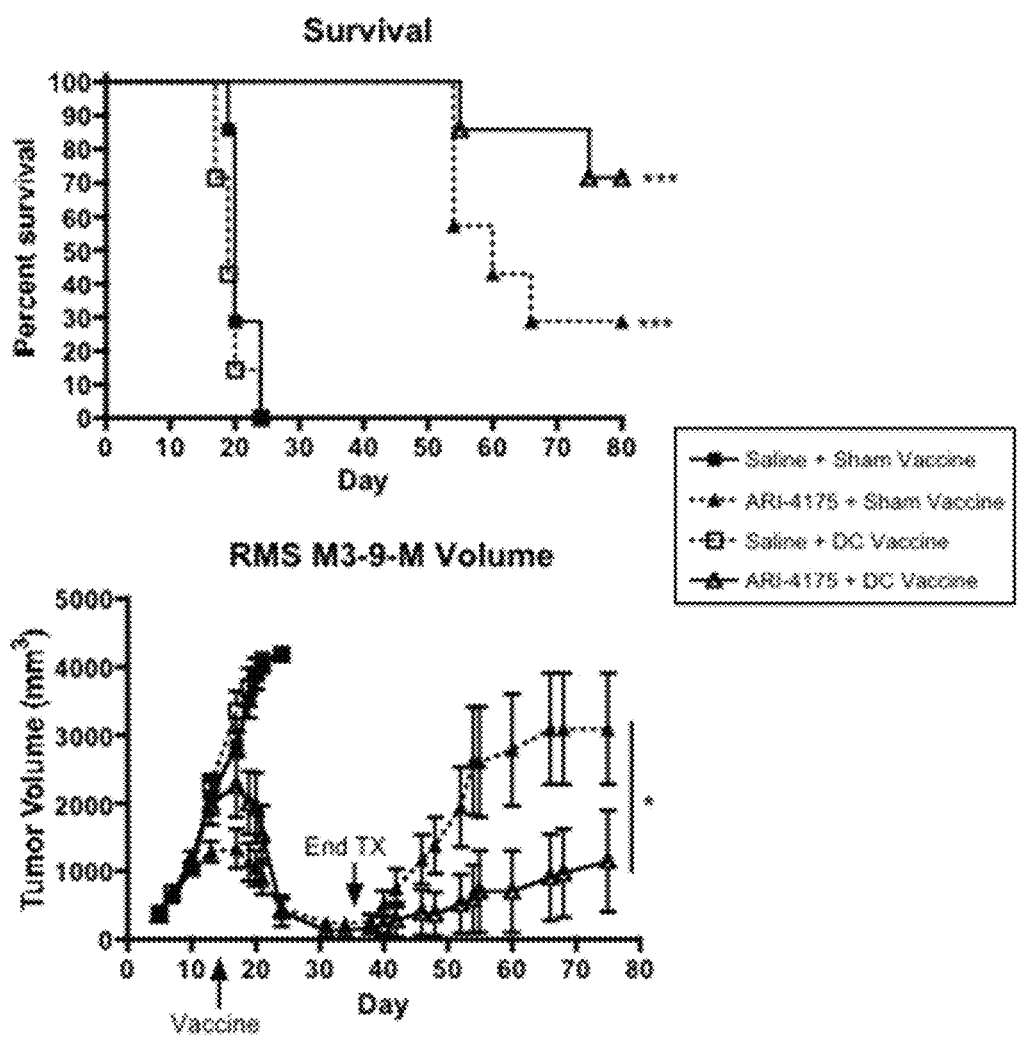

FIG. 19 A shows that ARI-4175 is a potent adjuvant to DC vaccination as evidenced by significantly improved survival and reduced RMS M3-9-M volume. The figure shows a late treatment model for DC vaccination and ARI-4175 treatment.

FIG. 19 B shows that ARI-4175 is a potent adjuvant to DC vaccination as evidenced by significantly improved survival and reduced RMS M3-9-M volume. The figure shows the tumor volume curve (mean±S.D.) and survival curve.

Figure 20:
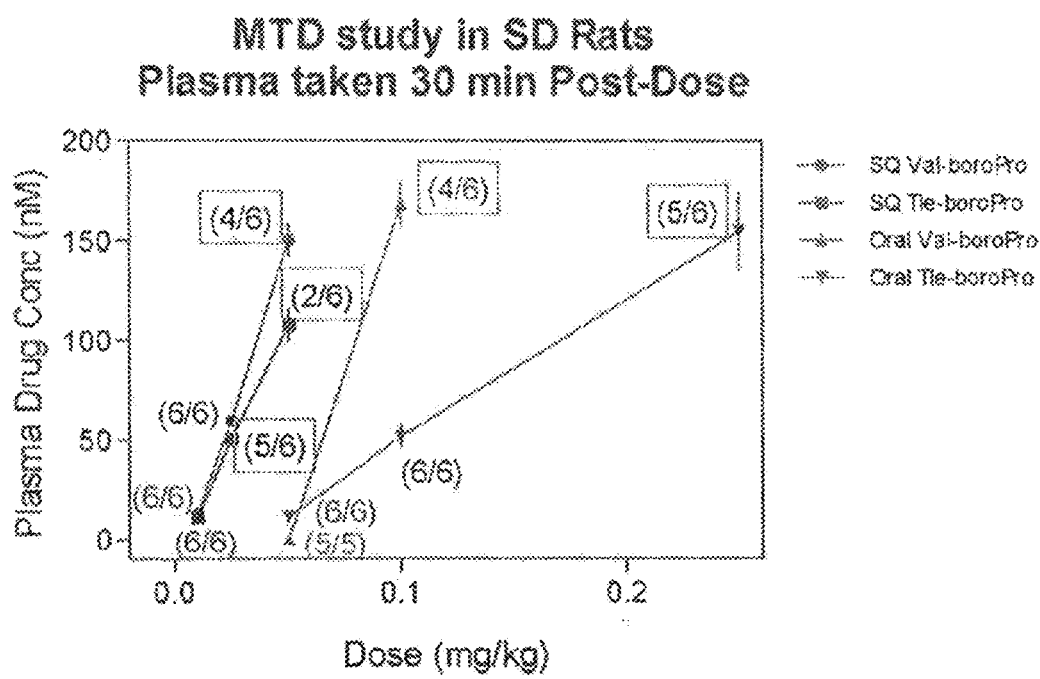

FIG. 20 shows the results of a maximum tolerated dose (MTD) study using SD rats with the data taken 30 minutes post-dose.

Figure 21:
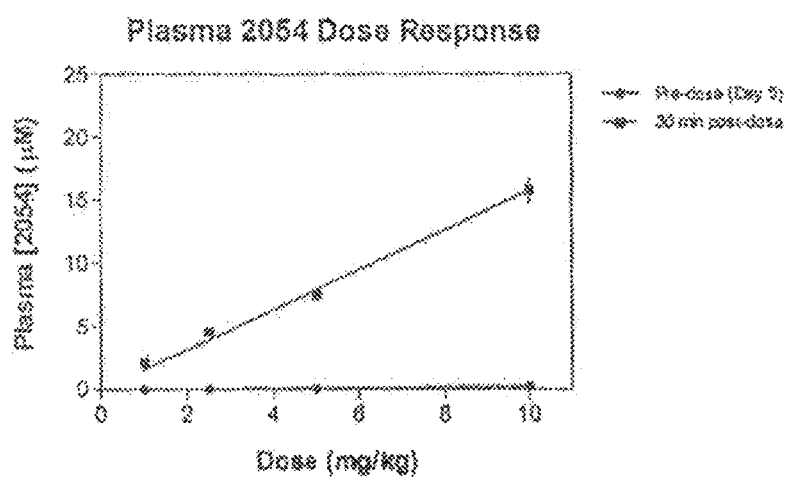
Figure 21:
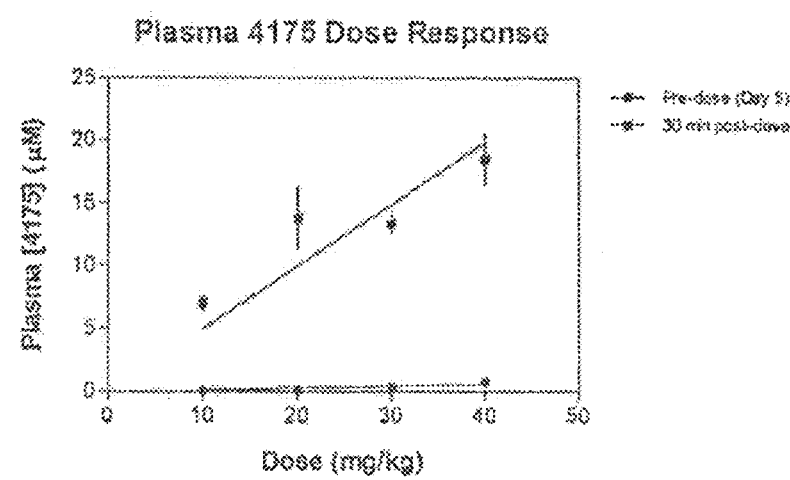

FIG. 21 shows a dose-plasma response curve for PT-100 and ARI-4175.

Figure 22:
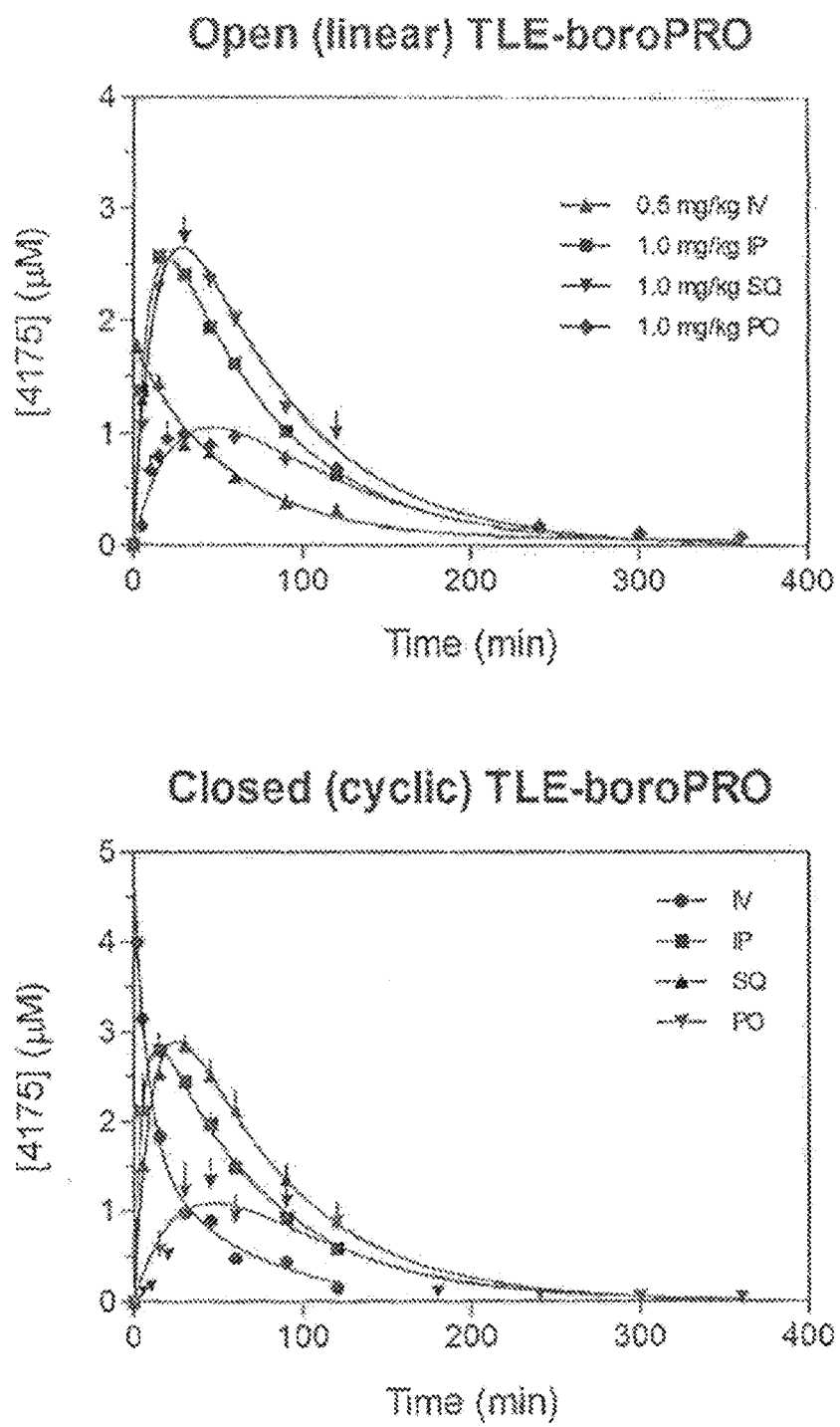

FIG. 22 shows pharmacokinetic data for the open vs. closed forms of ARI-4175. Under acidic conditions, ARI-4175 exists in an open, or linear, form; under neutral or basic conditions, a closed, cyclized form is highly favored.

Figure 23:
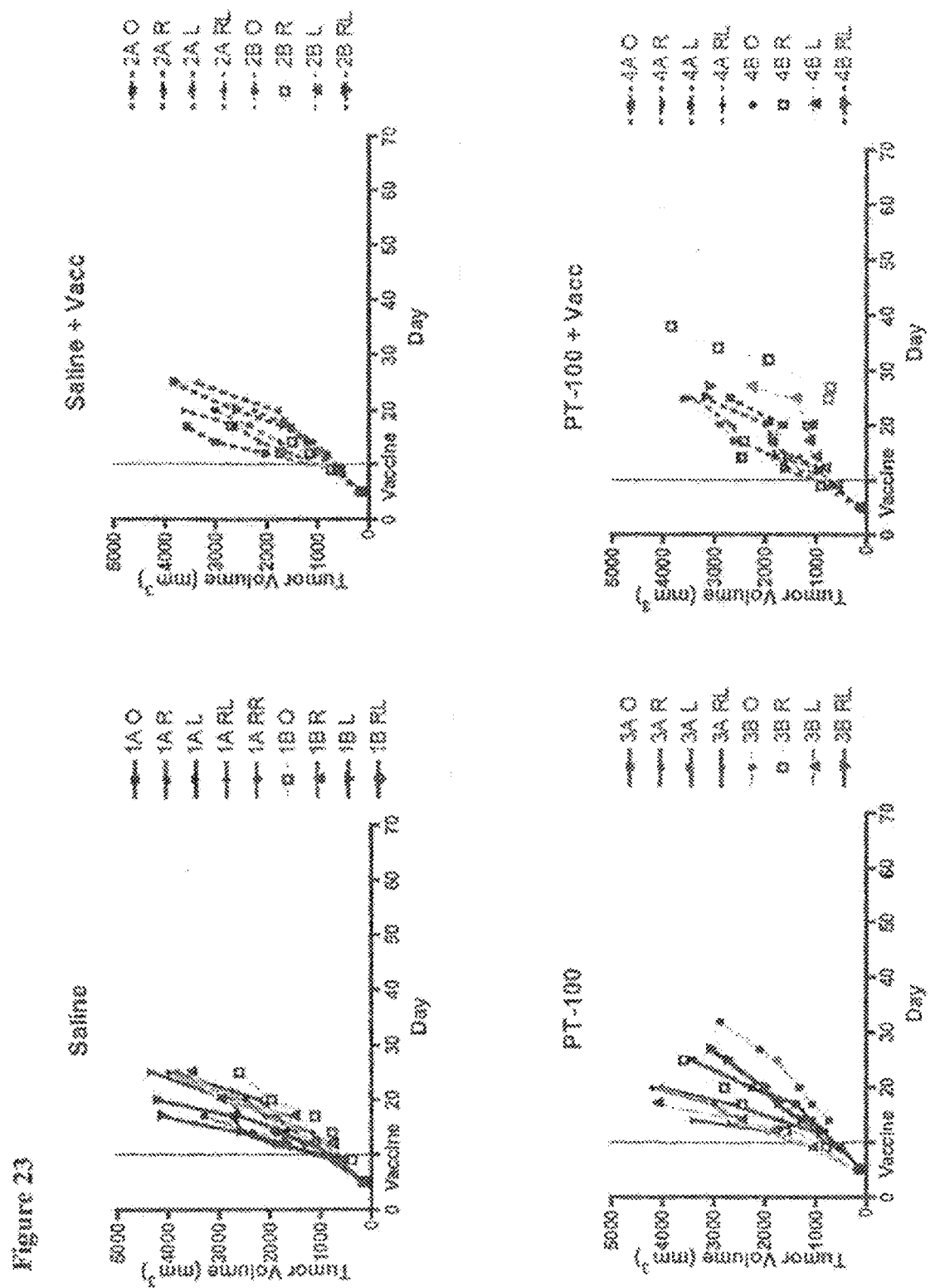
Figure 23:
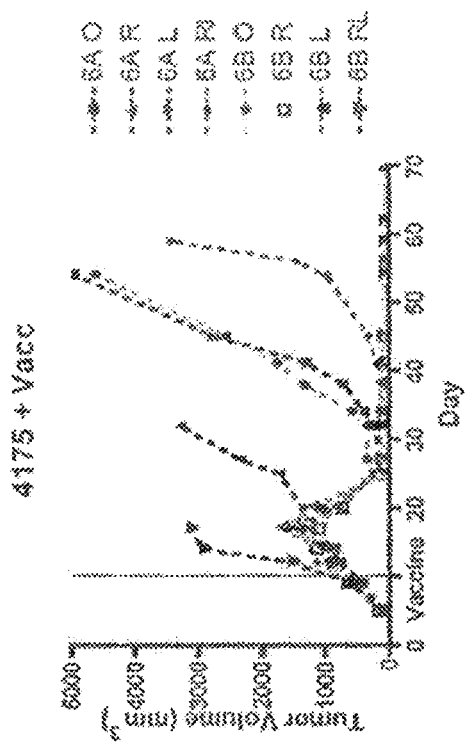
Figure 23:
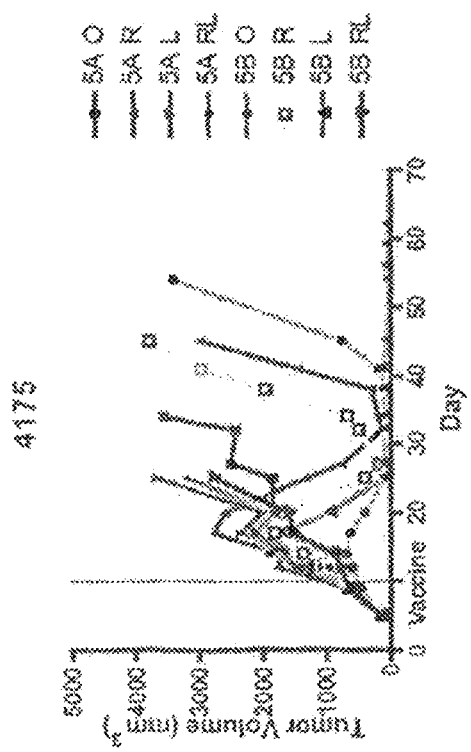

FIG. 23 shows tumor growth in individual mice in the RMS model.

DETAILED DESCRIPTION OF THE INVENTION

One aspect of the present invention relates to a method of treating cancer, comprising administering to a mammal in need thereof a therapeutically effective amount of a compound that inhibits a plurality of mammalian DASH serine proteases.

Another aspect of the present invention relates to a method of treating cancer, comprising administering to a mammal in need thereof a therapeutically effective amount of a compound that inhibits a plurality of mammalian DASH serine proteases, wherein the compound is not Val-boroPro.

Another aspect of the present invention relates to any one of the foregoing methods, wherein said compound induces the production of a cytokine selected from the group consisting of GCSF and CXCL1.

Another aspect of the present invention relates to any one of the foregoing methods, wherein the cancer is selected from the group consisting of basal cell carcinoma, biliary tract cancer, bladder cancer, bone cancer, brain cancer, breast cancer, cervical cancer, choriocarcinoma, CNS cancer, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, acute myeloid leukemia, acute lymphoid leukemia, chronic myeloid leukemia, chronic lymphoid leukemia, liver cancer, small cell lung cancer, non-small cell lung cancer, lymphoma, Hodgkin's lymphoma, Non-Hodgkin's lymphoma, melanoma, myeloma, neuroblastoma, oral cavity cancer, ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancer of the urinary system.

In other embodiments, the cancer is selected from the group consisting of prostate cancer, colorectal cancer, multiple myeloma, and non-small cell lung cancer.

In certain other embodiments, the cancer is selected from lung cancer, colorectal cancer, breast cancer, pancreatic cancer and prostate cancer.

In one embodiment, the cancer is lung cancer.

In another embodiment, the cancer is non-small cell lung cancer.

In yet another embodiment, the cancer is colorectal cancer.

In certain embodiments, the cancer is breast cancer.

In certain other embodiments, the cancer is pancreatic cancer.

In another embodiment, the cancer is prostate cancer.

In certain embodiments, the cancer is metastatic.

Another aspect of the invention relates to any one of the methods described above, further comprising co-administering to the mammal a therapeutically effective amount of tumor-primed T-cells.

In certain embodiments, the tumor-primed T-cells are administered prior to the administration of the compound.

In certain embodiments, the tumor-primed T-cells are administered subsequent to the administration of the compound.

In certain embodiments, the tumor-primed T-cells are administered concurrently with administration of the compound.

Another aspect of the invention relates to any one of the methods described above, further comprising co-administering to the mammal a therapeutically effective amount of an orally active tumor antigen.

Yet another aspect of the invention relates to any one of the methods described above, further comprising co-administering to the mammal a therapeutically effective amount of a dendritic cell vaccine.

Still another aspect of the invention relates to any one of the methods described above, further comprising administration of an adjuvant.

Another aspect of the present invention relates to any one of the aforementioned embodiments, further comprising treating the mammal with a second therapy selected from the group consisting of surgery, radiation and chemotherapy.

In one embodiment, the second therapy is surgery.

In another embodiment, the second therapy is radiation.

In yet another embodiment, the second therapy is chemotherapy.

In certain embodiments, the chemotherapy is selected from the group consisting of of ipilimumab, vemurafenib, GDC-0879, PLX-4720, aldesleukin, asparaginase, bleomycin sulfate, carboplatin, chlorambucil, cisplatin, cladribine, cyclophosphamide, cytarabine, dacarbazine, dactinomycin, daunorubicin hydrochloride, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-α2a, interferon-α2b, interferon-αn3, interferon-α1b, interleukins, irinotecan, mechlorethamine hydrochloride, melphalan, mercatopurine, methotrexate, methotrexate sodium, mitomycin, mitoxantrone, paclitaxel, pegaspargase, pentostatin, prednisone, profimer sodium, procabazine hydrochloride, taxol, taxotere, teniposide, topotecan hydrochloride, vinblastine sulfate, vincristine sulfate and vinorelbine tartrate.

In certain embodiments the chemotherapy is selected from the group consisting of bleomycin sulfate, carboplatin, cisplatin, docetaxel, doxorubicin, doxorubicin hydrochloride, fluorouracil, gemcitabine, gemcitabine hydrochloride, methotrexate, methotrexate sodium, paclitaxel, taxol, taxotere, vinblastine sulfate and vincristine sulfate.

In certain embodiments, the chemotherapy is a dipeptidylpeptidase IV inhibitor.

In certain other embodiments, the chemotherapy is a FAP-activated chemotherapeutic, a FAP-activated dipeptidylpeptidase IV inhibitor, or a FAP-activated proteasome inhibitor.

In still other embodiments, the chemotherapy is a FAP-activated proteasome inhibitor.

In certain embodiments, the chemotherapy is an antibody.

In certain other embodiments, the antibody is selected from the group consisting of trastuzamab, cetuximab, bevacizumab, and rituximab.

One aspect of the present invention relates to a method of increasing antitumor immunity in a mammal, comprising administering to a mammal in need thereof an effective amount of a compound that inhibits a plurality of mammalian DASH serine proteases.

In certain embodiments, the compound is not Val-boro-Pro.

In certain other embodiments, the compound induces the production of a cytokine selected from the group consisting of GCSF and CXCL1.

In yet other embodiments, the antitumor immunity is increased for tumors selected from the group consisting of lung tumors, lymphomas, breast tumors, colorectal tumors, thyroid tumors, uterine tumors, pancreatic tumors, prostate tumors, skin tumors, kidney tumors, liver tumors and brain tumors.

In other embodiments, the antitumor immunity is increased for tumors selected from the group consisting of lung tumors, breast tumors, colorectal tumors, pancreatic tumors and prostate tumors.

In certain other embodiments, the antitumor immunity comprises antibody-dependent cell-mediated cytotoxicity.

Another aspect of the invention relates to a method of stimulating or enhancing an immune response in a mammal, comprising administering to a mammal in need thereof an effective amount of a compound that inhibits a plurality of mammalian DASH serine proteases.

In certain embodiments, the compound is not Val-boro-Pro.

In certain other embodiments, the compound induces the production of a cytokine selected from the group consisting of GCSF and CXCL1.

In still other embodiments, the immune response is stimulated.

In still yet further embodiments, the immune response is enhanced.

In certain embodiments, the immune response comprises antibody-dependent cell-mediated cytotoxicity.

In certain other embodiments, the mammal has cancer or is at risk of developing cancer.

In still other embodiments, the mammal is in remission of cancer.

In still yet further embodiments, the mammal has a refractory or resistant cancer.

Another aspect of the invention relates to a method of treating a condition characterized by abnormal cell proliferation, comprising administering to a mammal in need thereof a therapeutically effective amount of a compound that inhibits a plurality of mammalian DASH serine proteases.

In certain embodiments, the compound is not Val-boro-Pro.

In certain embodiments, the compound induces the production of a cytokine selected from the group consisting of GCSF and CXCL1.

In certain embodiments, the abnormal cell proliferation is cancer, a blood vessel proliferative disorder or a fibrotic disorder.

In certain embodiments, the abnormal cell proliferation is abnormal angiogenesis.

Another aspect of the invention relates to a method of increasing cytokine and/or chemokine production in a mammal, comprising administering to a mammal in need thereof an effective amount of a compound that inhibits a plurality of mammalian DASH serine proteases.

In certain embodiments, the compound is not Val-boro-Pro.

In certain other embodiments, the compound induces the production of a cytokine selected from the group consisting of GCSF and CXCL1.

Another aspect of the invention relates to a method of stimulating or enhancing production of T-cells in a mammal, comprising administering to a mammal in need thereof an effective amount of a compound that inhibits a plurality of mammalian DASH serine proteases, wherein said T-cells recognize an antigen on a malignant cell.

In certain embodiments, the compound is not Val-boro-Pro.

In certain other embodiments, the compound induces the production of a cytokine selected from the group consisting of GCSF and CXCL1.

In certain other embodiments, the production of T-cells is stimulated.

In yet other embodiments, the production of T-cells is enhanced.

In still yet other embodiments, the malignant cell is a carcinoma, sarcoma, leukemia, lymphoma or myeloma.

In certain embodiments, the mammal is a primate, canine, equine, feline or bovine.

In certain other embodiments, the mammal is a human.

In certain embodiments, the compound is administered orally or parenterally.

In certain other embodiments, the compound is administered parenterally.

In yet other embodiments, the compound is administered orally.

In certain embodiments, the compound is administered in a solid dosage form.

In certain other embodiments, the solid dosage form is a tablet, capsule or pill.

In yet other embodiments, the solid dosage form is a tablet.

In certain embodiments, the compound is administered in an amount sufficient to stimulate the immune system without dose limiting toxicity.

In certain embodiments, the invention relates to any one of the methods described above, wherein the compound is represented by Formula I:

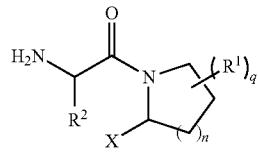

Formula I wherein:
X is $B(Y^1)(Y^2)$ or CN;
$Y^1$ and $Y^2$ are independently OH, or together with the boron atom to which they are attached represent a group that is hydrolysable to a boronic acid, or together with the boron atom to which they are attached form a 5- to 8-membered ring that is hydrolysable to a boronic acid;
$R^1$ is selected from the group consisting of halogen, lower alkyl, lower alkenyl, lower alkynyl, carbonyl, carboxyl, ester, formate, ketone, thiocarbonyl, thioester, thioacetate, thioformate, amino, acylamino, amido, nitro, sulfate, sulfonate, sulfonamido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, or —$(CH_2)_n$—S—$(CH_2)_m$—$R_7$, azido, cyano, isocyanato, thiocyanato, isothiocyanato, cyanato, —N≡C⊕⊖, or —C≡C—$R_8$;

$R_7$ represents a substituted or unsubstituted aryl, aralkyl, cycloalkyl, cycloalkenyl, or heterocycle;
$R_8$ independently represents hydrogen, —$CH_3$, or —$(CH_2)_n$—$CH_3$;
m is 0, 1, 2, 3, 4, 5, or 6;
$R^2$ is a hydrophobic group selected from the group consisting of n-propyl, $C_4$-$C_8$ alkyl, $C_2$-$C_8$alkenyl, $C_2$-$C_8$alkynyl, $C_3$-$C_8$cycloalkyl, $C_2$-$C_7$heterocyclyl, aryl, heteroaryl, aralkyl, heteroaralkyl, and side chains of naturally occurring hydrophobic amino acids;
n is 0, 1, or 2; and
q is 0, 1, 2, 3, or 4.
In certain embodiments, q is 0, 1, or 2.
In certain other embodiments, q is 0.
In yet other embodiments, n is 0.
In still yet other embodiments, n is 1.
In certain other embodiments, n is 2.
In certain embodiments, X is $B(Y^1)(Y^2)$.
In certain other embodiments, X is $B(OH)_2$.
In certain embodiments, n is 1; q is 0; and X is $B(OH)_2$.
In certain embodiments, $R^2$ is selected from the group consisting of t-butyl, isobutyl, pentyl, cyclohexyl, benzyl, or naphthyl.
In certain other embodiments, $R^2$ is selected from the group consisting of t-butyl, isobutyl, or pentyl.
In still yet other embodiments, $R^2$ is t-butyl.
In certain embodiments, $R^2$ is the side chain of a naturally occurring hydrophobic amino acid.
In certain other embodiments, $R^2$ is the side chain of leucine, isoleucine, tert-leucine, phenylalanine, or tryptophan.
In certain embodiments, the compound of Formula I is t-butylGly-boroPro.
In certain embodiments, the stereochemical configuration at the carbon bearing X is L.

In certain other embodiments, the stereochemical configuration at the carbon bearing X is D.

In certain embodiments, the stereochemical configuration at the carbon bearing $R^2$ is L.

In certain other embodiments, the stereochemical configuration at the carbon bearing $R^2$ is D.

In certain embodiments, the stereochemical configuration at the carbon bearing X is L; and the stereochemical configuration at the carbon bearing $R^2$ is L.

In certain other embodiments, the stereochemical configuration at the carbon bearing X is L; and the stereochemical configuration at the carbon bearing $R^2$ is D.

In yet other embodiments, the stereochemical configuration at the carbon bearing X is D; and the stereochemical configuration at the carbon bearing $R^2$ is L.

In certain embodiments, the stereochemical configuration at the carbon bearing X is D; and the stereochemical configuration at the carbon bearing $R^2$ is D.

The term "DASH serine protease" means dipeptidyl peptidase (DPP) IV activity and/or structural homologues thereof. These proteins are enzymes that are united by their common post-proline-cleaving serine dipeptidase mechanism. For example, DPP-VII, originally named quiescent cell proline dipeptidase (QPP), is a DASH serine protease.

Val-boroPro, also known as PT-100 or talabostat, appears to stimulate immunity via the activation of caspase-1 and induction of IL-1β in macrophages, which in turn upregulates cytokine and chemokine expression in macrophages and stromal fibroblasts. Intracellular DPP 8 and/or 9 activity appears to be the relevant target for PT-100 in macrophages. This mechanism of action indicates a hitherto unforeseen regulatory role for intracellular DPPs in the immune system.

ARI-4175, tertiary-butyl (abbreviated t-butyl) Gly-boro-Pro, is a dipeptide boronic acid that potently inhibits all six members of the prolyl peptidase family of serine proteases as an adjuvant for dendritic cell vaccines for the treatment of cancer. Similarly to PT-100, ARI-4175 inhibits DPP8/9 activity. Other dipeptide boronic acids, preferably with a bulky, hydrophobic side chain such as isoleucine-boroPro, butylglycine-boroPro, phenylalanine-boroPro (Phe-boro-Pro), and cyclohexylglycine-boroPro (Cyg-boroPro) are expected to perform in a similar way. Routine experimentation by one skilled in the art could determine which compounds that inhibit a plurality of mammalian DASH serine proteases (e.g., compounds of Formula I) could be used successfully in the claimed methods.

PT-100 activates tumor immunity in mice via cytokine/chemokine upregulation in tumors and draining lymph nodes. The use of cytokines as cancer vaccine adjuvants is not new: e.g., GM-CSF for sipuleucel-T and GM-CSF or IL-2 and IFN-γ for vaccines in development. However, in comparison to these applications, the orally active DPP8/9 inhibitors, PT-100 and ARI-4175, have the advantage of stimulating tumor-associated macrophages and stromal cells to produce a combination of cytokines and chemokines that can cooperate to activate tumor-specific effector T cells. Among the cytokines and chemokines upregulated by PT-100, IL-1β, CXCL9 and CXCL10 are particularly noteworthy. IL-1β produced by tumor-associated macrophages plays a pivotal role in activating proinflammatory responses and in promoting development of $T_h17$ cells in the tumor microenvironment.

Based on strong preclinical antitumor activity and a novel mechanism of action, PT-100 was advanced into human trials in cancer and granted fast-track designation by the FDA. However, despite some signals of clinical activity in non-randomized Phase II studies of non-Hodgkin's lymphoma (NHL), metastatic melanoma and non-small cell lung cancer (NSCLC), PT-100 ultimately failed to meet its goals in pivotal Phase III trials in NSCLC. Two factors are likely to have contributed to this failure. Most importantly, pre-clinical studies indicated that for optimal antitumor activity of PT-100 in mice, an endogenous immune response to the tumor is required. It was unlikely that any such underlying tumor immunity remained in the late-stage NSCLC patients studied in Phase III. Secondly, dose-limiting toxicity in cancer patients appeared to prevent administration of high enough PT-100 doses for consistent immune stimulation patient to patient. The studies by Fry et al. suggest that PT-100's mechanism of action should be most effective clinically when employed to boost cancer vaccines. It is possible that PT-100 might be clinically successful when used with an appropriate vaccine that can prime tumor-specific T cells; but it is the goal of the present invention to identify an analog with lower toxicity that will achieve clinical success in humans.

ARI-4175 or other compounds that inhibit a plurality of mammalian DASH serine proteases (e.g., compounds of Formula I), alone or in combination with dendritic cell therapy (DCT), trastuzumab, cetuximab, ipilimumab, vemurafenib, sorafenib, or other cancer immunotherapies, have a significant advantage over other cancer immunotherapies because they are orally active small molecules. They elicit immune activation similar to difficult and expensive DCT or antibody treatments, but can be administered much more easily. ARI-4175 and compounds that inhibit a plurality of mammalian DASH serine proteases (e.g., compounds of Formula I) are the first "orally active tumor antigens" of their kind.

Many patients do not respond to cetuximab, or develop resistance after initial response to therapy. This is due to the cancer developing resistance to the immune system of the patient. The immune response is still present, but is either no longer strong enough to kill the tumor or the tumor becomes invisible to the immune system. One example is the KRAS mutation found in approximately 40% of malignant colorectal cancers. A recent clinical trial (Lievre et al., Cancer Res. 2006, 66 (8), 3992) found that KRAS mutations were correlated with resistance to cetuximab, while all of the patients who responded to cetuximab lacked the KRAS mutation. Although the molecular mechanisms by which cetuximab produces a clinical response remain unknown, re-activation of the immune response with ARI-4175 may, alone or in combination with cetuximab or other immunotherapies, improve clinical outcomes in patients whose immune response is insufficient to kill the tumor or who have a refractory cancer.

ARI-4175 or other compounds that inhibit a plurality of mammalian DASH serine proteases (e.g., compounds of Formula I) may also be used in combination with T cell adoptive transfer therapies. This treatment method uses T-cell-based cytotoxic responses to attack cancer cells. The adjuvant properties of ARI-4175 would allow it to be used as a pre-treatment before administration of tumor-infiltrating lymphocytes, or TIL, or as a post-treatment after administration of adoptive cell transfer.

The low toxicity of ARI-4175 (or other compounds that inhibit a plurality of mammalian DASH serine proteases (e.g., compounds of Formula I) allows it to be used as an adjuvant in cancer patients whose cancer is currently in remission. Such patients would benefit from an increased anti-tumor immune response to avoid relapse.

It is expected that ARI-4175 and other compounds that inhibit a plurality of mammalian DASH serine proteases (e.g., compounds of Formula I) would perform synergistically with CTLA4 inhibitors, such as ipilimumab (Yervoy®), which is a receptor antagonist that increases immune activity. The CTLA4 (cytotoxic T lymphocyte antigen 4), also known as CD152, is a protein receptor that downregulates the immune system. ARI-4175 or other compounds that inhibit a plurality of mammalian DASH serine proteases (e.g., compounds of Formula I) in combination with CD28 receptor agonists would work in a similar way to increase the activity of T cells.

EXEMPLIFICATION

The invention now being generally described, it will be more readily understood by reference to the following examples which are included merely for purposes of illustration of certain aspects and embodiments of the present invention, and are not intended to limit the invention.

Example 1

Rationale, Synthesis of Compounds, and Inhibition of RMS Tumor Growth

Synthesis of ARI-4175. Commercially available L-boroPro-pn 2 was coupled to an N-Boc protected unnatural amino acid Boc-Tle-OH 3 (CAS NO 62965-35-9) using HATU to render a protected dipeptide boronate Boc-Tle-boroPro-pn. Concurrent removal of both protection groups by trichloroborane (BCl$_3$) followed by reverse-phase HPLC purification yields the desired product 1 (ARI-4175) as an HCl salt.

Scheme 1. Synthetic scheme for ARI-4175. Reagents and conditions: (i) Boc-L-Tle-OH, HATU/DIPEA/DMF, (ii) BCl$_3$.

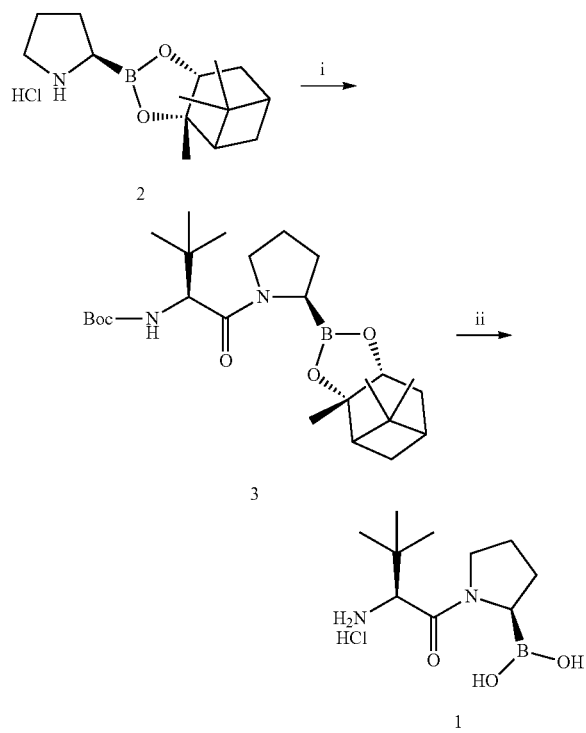

Synthesis of PT-100. PT-100 was synthesized as previously described in sufficient quantities for the studies described in the following examples.

ARI-4175 is a nanomolar inhibitor of the DPP-IV-like serine proteases, including DPPs 8 and 9 (Table 1), which are the putative targets in PT-100's immune mechanism of action. Inhibition of DPP-IV and FAP activity may also contribute to the antitumor effect of PT-100 because selective abrogation of DPP-IV or FAP activity appears to slow tumor growth.

TABLE 1

Potency of inhibition of DPP-IV-like protease activities in vitro

| Inhibitor | $IC_{50}$[1] (nM) | | | | | |
|---|---|---|---|---|---|---|
|  | DPP-IV | DPP8 | DPP9 | DPP-II | FAP | PREP[2] |
| PT-100 (Val-boroPro) | 0.7 | 3.6 | 1.7 | 8.2 | 17.0 | 35.0 |
| ARI-4175 (t-butylGly-boroPro) | 1.6 | 5.1 | 1.9 | 88.0 | 32.0 | 24.0 |

[1]50% mean inhibitory concentration
[2]Prolyl endopeptidase

C57BL/6 mice bearing established RMS were vaccinated intramuscularly in a hind limb with RMS DC vaccine on day 10 after tumor inoculation. ARI-4175, PT-100 or vehicle was administered by daily gavage from day 10 onwards for 3 cycles of 5 days each as described herein: ARI-4175, 10 mg/kg, cycle 1 and 5 mg/kg cycles 2 and 3; PT-100, 1 mg/kg cycles 1 to 3. Another group of mice received vaccine but no compounds and groups of unvaccinated mice received compounds or vehicle. 8 replicate mice were treated in each regimen.

Figure 1:
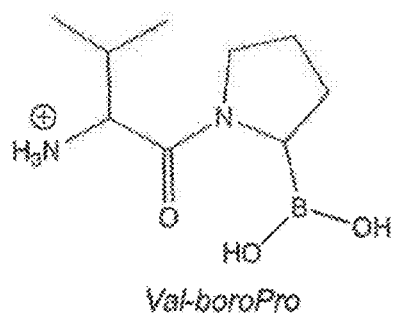
FIG. 1 shows that Ala-boroPro (A-bP) and Val-boroPro (V-bP) both inhibit prolyl oligoproteases, but Ala-boroPro does not stimulate the immune system. Val-boroPro is a potent immune stimulator.
Figure 1:
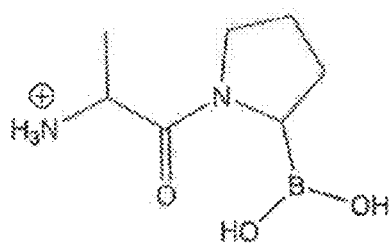
Figure 2:
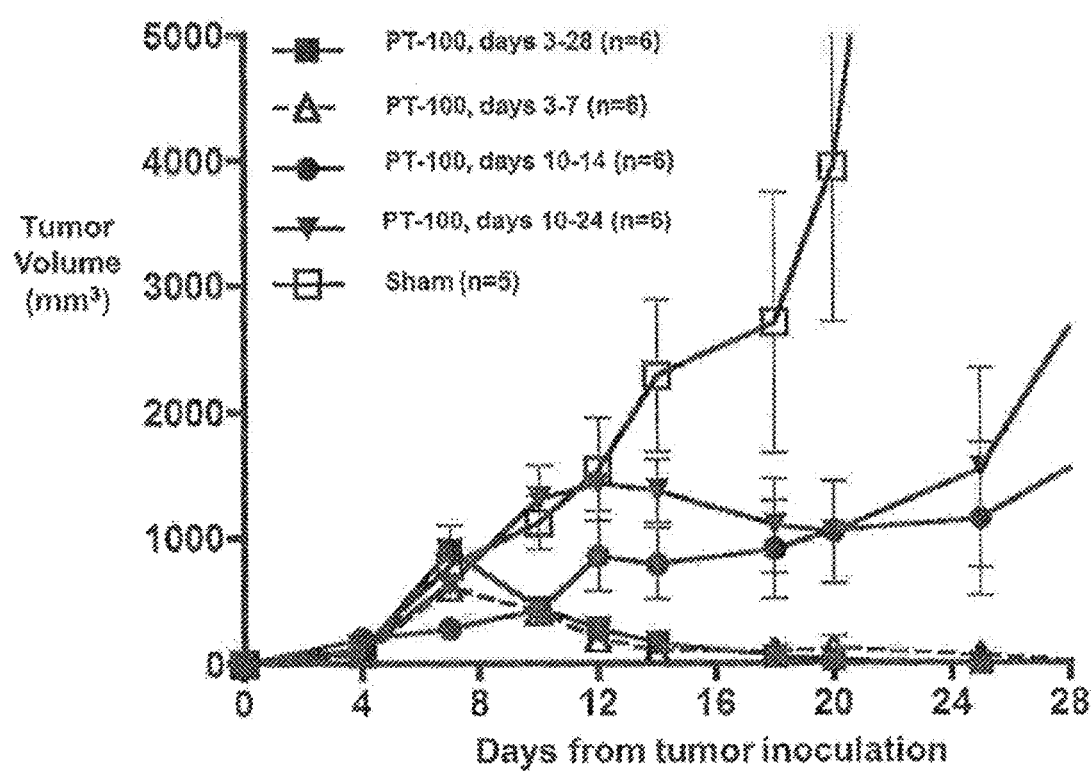
FIG. 2 shows that PT-100 produces complete regression of early stage tumors but not of established tumors.
Figure 3:
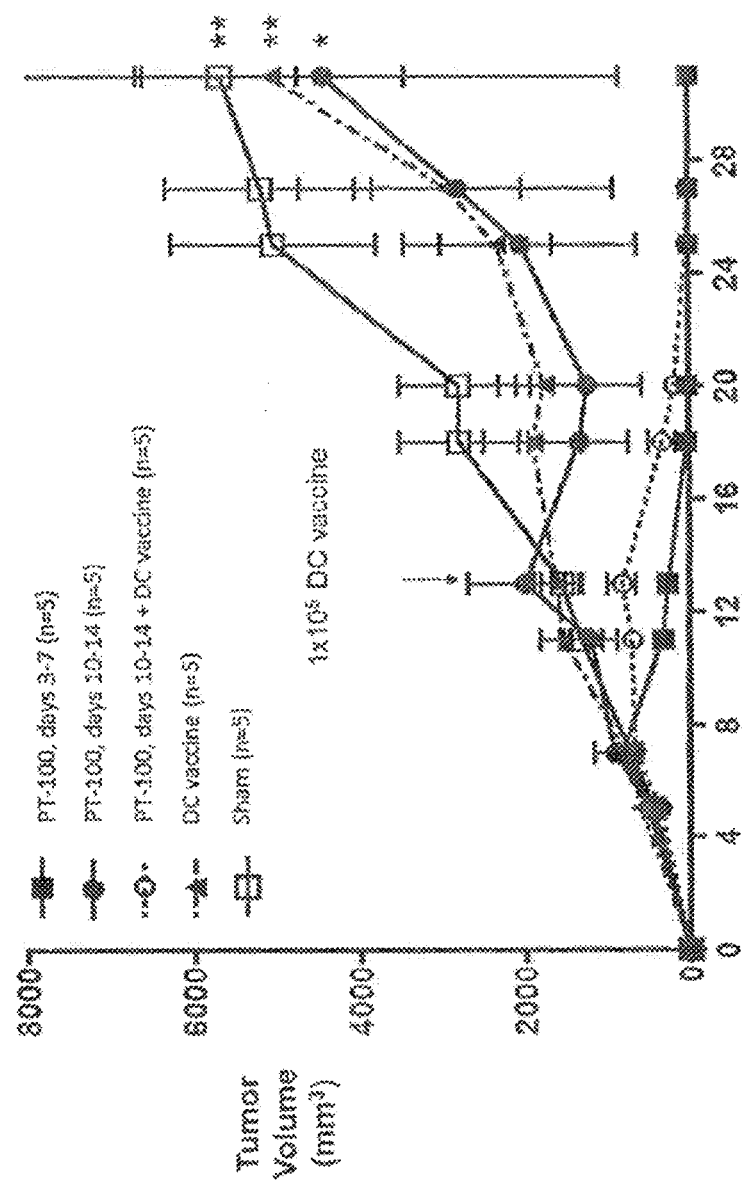
FIG. 3 shows that PT-100+Dendritic Cell (DC) vaccine produces regression of established tumors.
Figure 8A:
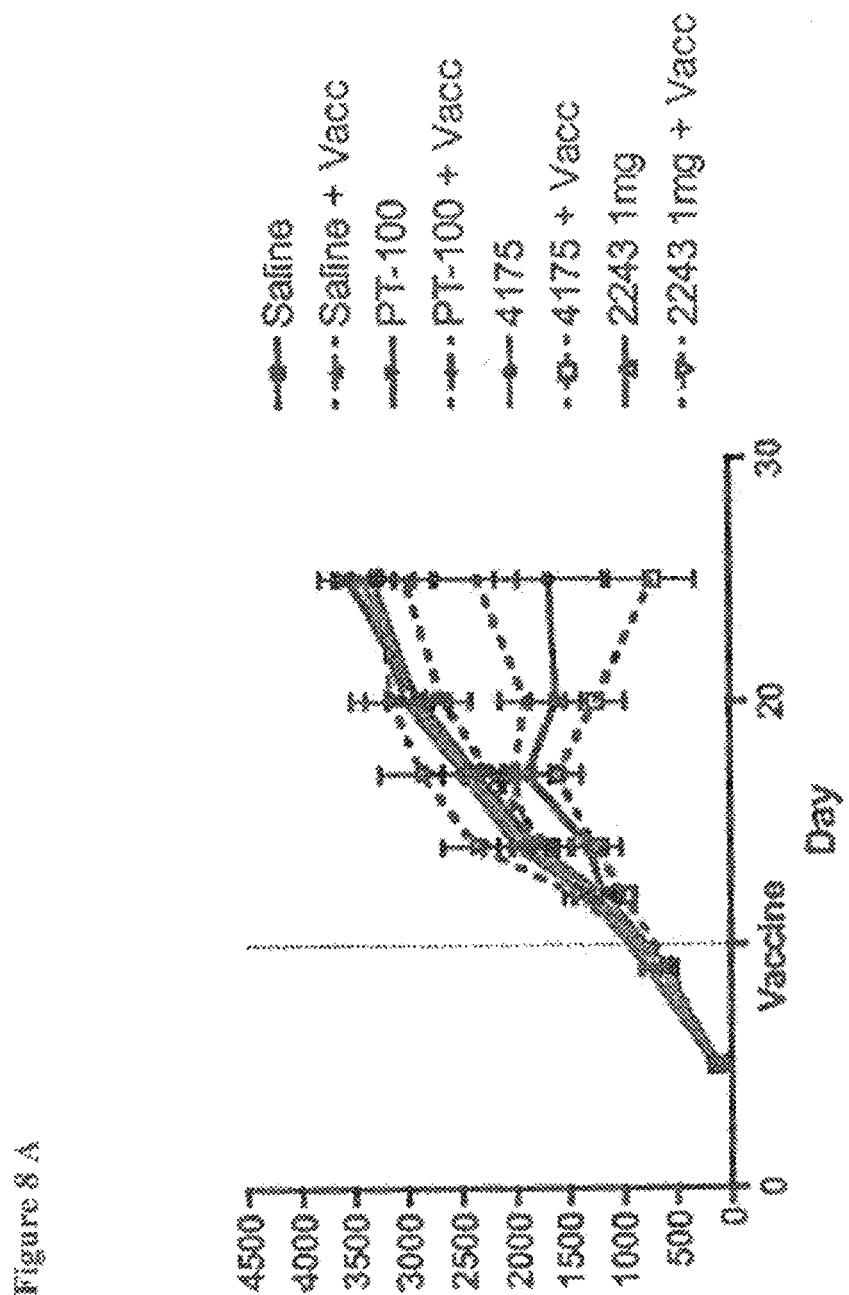
FIG. 8 A shows that ARI-4175 increases potency of a DC vaccine in a rhabdomyosarcoma (RMS) model to inhibit growth of established RMS. C57BL/6 mice were injected intramuscularly with RMS cells on day 0. Mice received a single subcutaneous vaccination on day 10 followed by daily gavage of 10 mg/kg (5 days) and 5 mg/kg (10 days) ARI-4175, 1 mg/kg PT-100 (15 days), or vehicle as described in Example 1.
Figure 8:
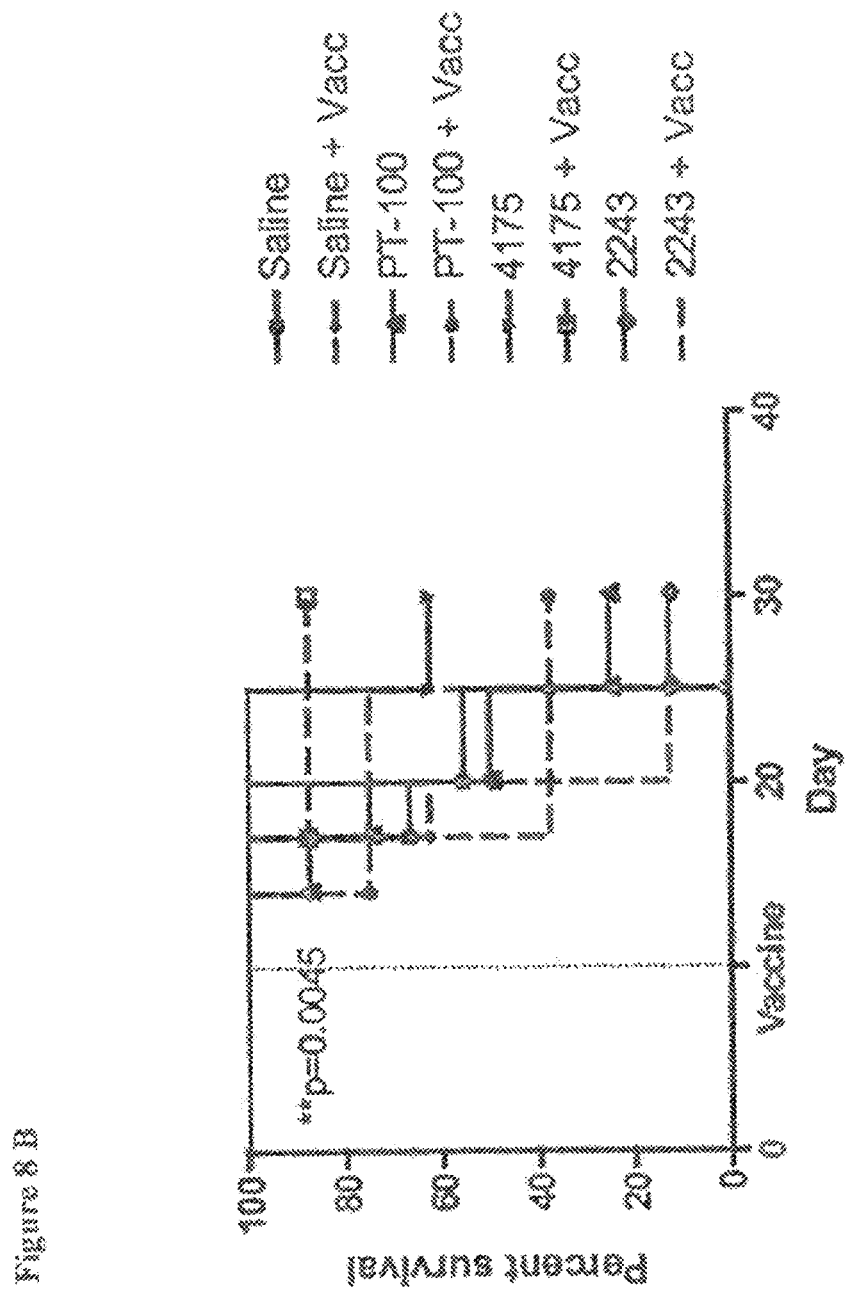
Figure 9:
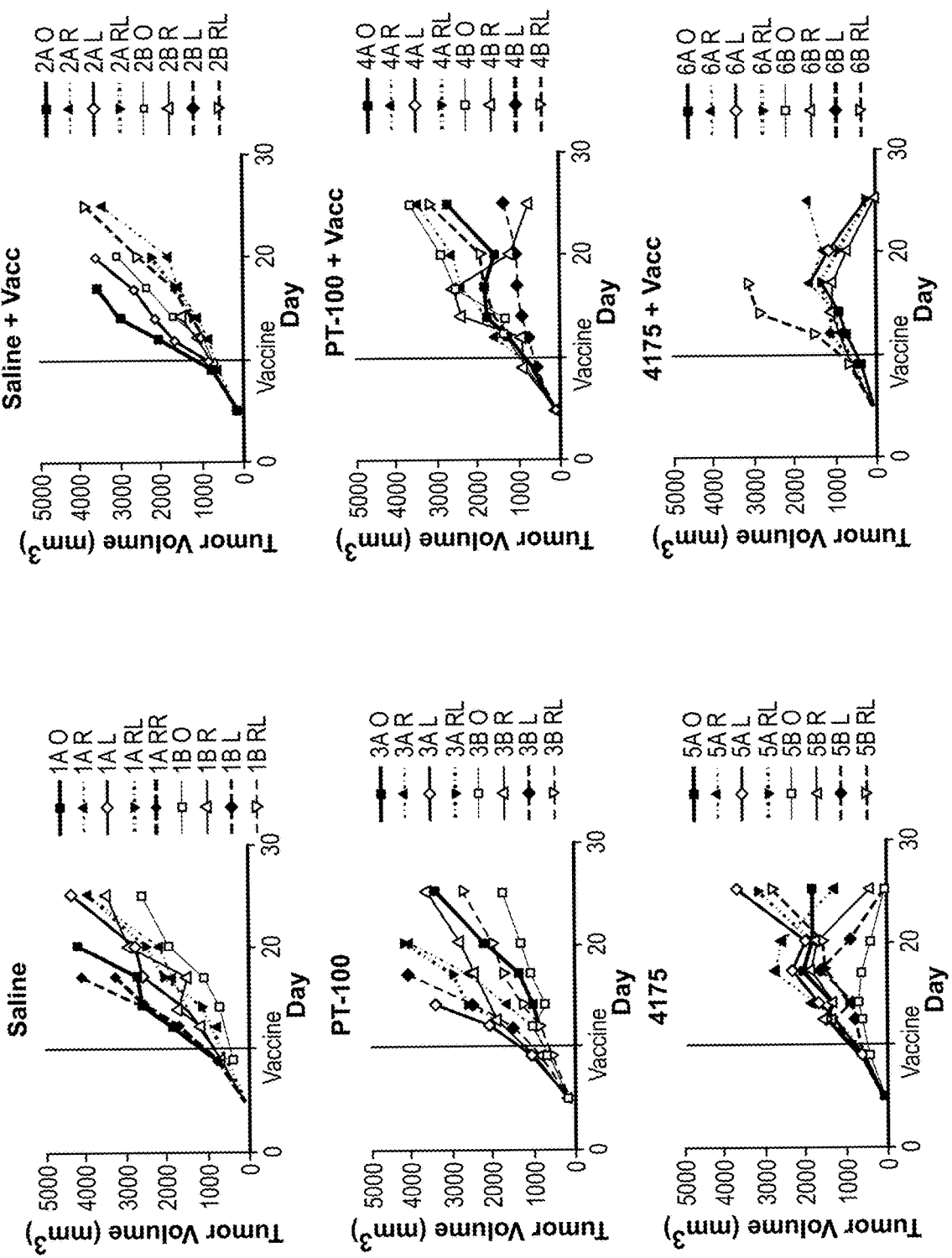
FIG. 9 shows tumor growth in individual mice in the experiment described in Experiment 1.

As shown in FIG. 8, administration of ARI-4175 by itself significantly slowed tumor growth (FIG. 8A) and produced tumor regression in 3/8 mice by day 25 (FIG. 9). In combination with vaccine, ARI-4175 produced regression in 6/8 mice (FIG. 9) and increased mouse survival significantly (P=0.0045; FIG. 1B). In contrast, PT-100 administered at a dose of 1 mg/kg, either with or without DC vaccination, failed to produce tumor regression (FIG. 2) by day 25 or significant inhibition of tumor growth (FIG. 8A), and tumor growth was only reduced in 2 out of 6 mice treated with PT-100 and the vaccine (FIG. 9). The 1 mg/kg dose of PT-100 was previously shown to be optimal for activation of tumor immunity in C57BL/6 mice, and the dose cannot be increased much higher because the MTD for PT-100 is ~2 mg/kg in C57BL/6 mice. Therefore, the significant vaccine adjuvant effect of a 10/5-mg/kg dose of ARI-4175 suggests that ARI-4175 is less toxic than PT-100, and that it is possible to increase the dose of ARI-4175 to achieve greater tumor regression and mouse survival than is possible with PT-100 at tolerated doses in the RMS mouse model.

Example 2

Effectiveness of ARI-4175 in the RMS DC Tumor Vaccine Model

Figure 17:
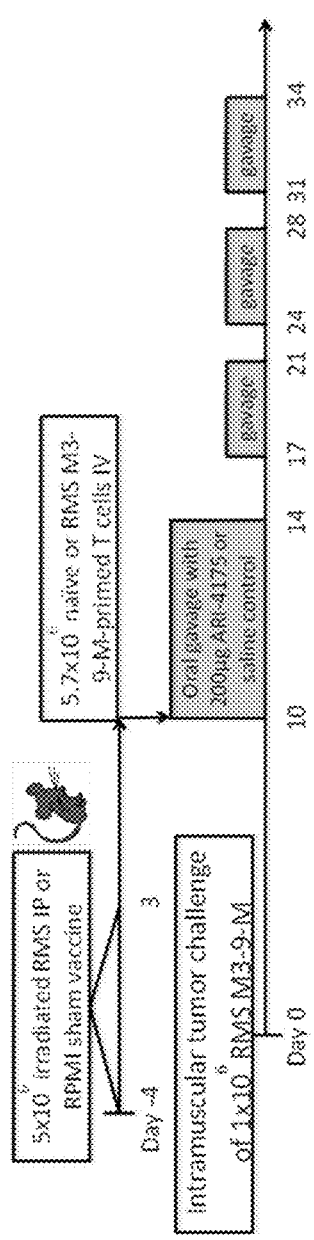
FIG. 17 A shows that as adjuvant to tumor-primed T cell transfer, ARI-4175 induces tumor regression in late treatment RMS M3-9-M model.
Figure 17:
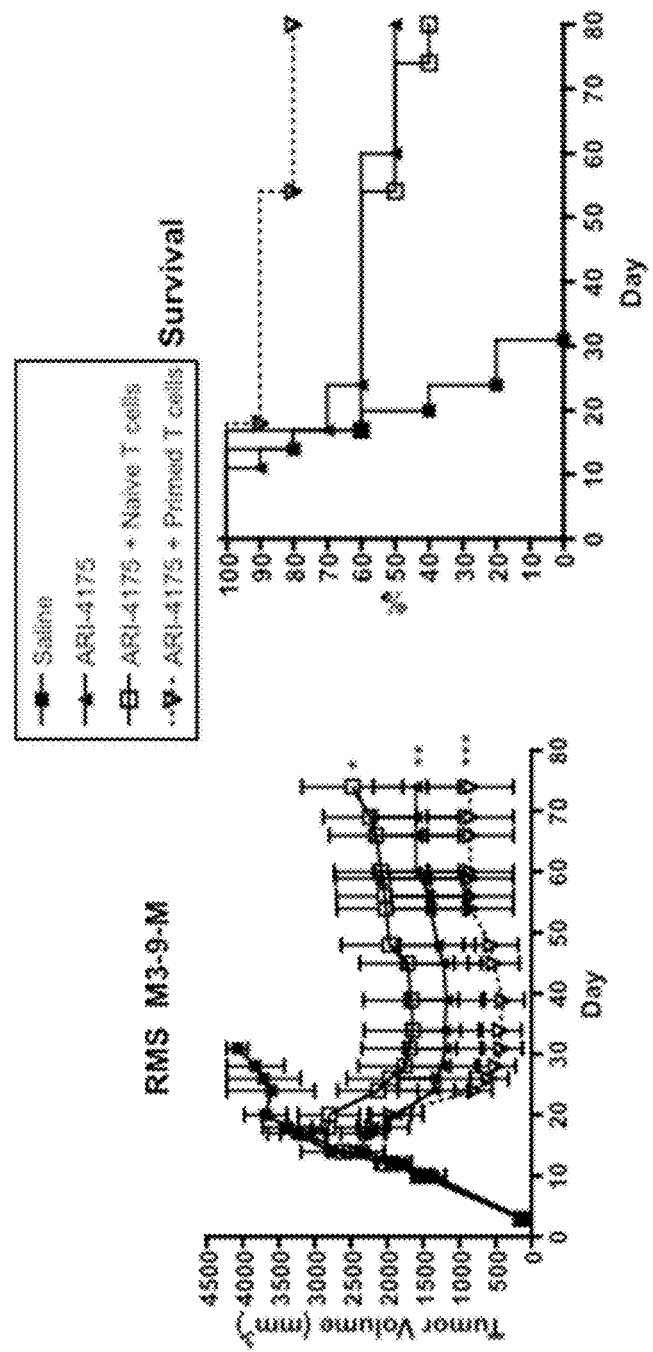

FIG. 17A shows the experimental setup for priming of T cell donors and T cell recipients. FIG. 17B shows the tumor volume curve (mean±standard deviation) and survival curve. Mice receiving ARI-4175 alone had significantly smaller tumors compared to saline (n=10, p=0.0019). Though ARI-4175+primed T cell recipients had smaller tumors, the difference was not significant when compared to ARI-4175+naïve T cell recipients (n=10, p=0.0755). Eight of ten ARI-4175+primed T cell recipients survived to day 80, however this was not significant compared to the 40% survival of ARI-4175+naïve T cell recipients (n=10, p=0.0658).

Figure 18:
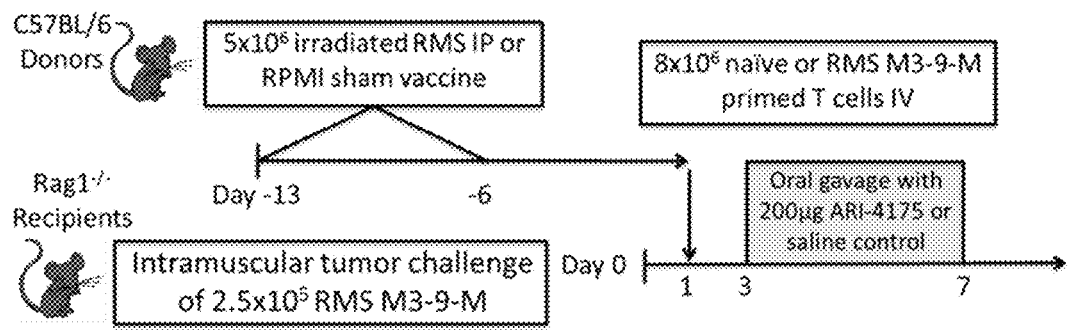
FIG. 18 A shows that combination treatment with ARI-4175 and adoptive T cell transfer in Rag1−/− recipients significantly reduces RMS M3-9-M volume: Female Rag1$^{-/-}$ mice received nave or RMS-primed T cells one day after tumor challenge.
Figure 18:
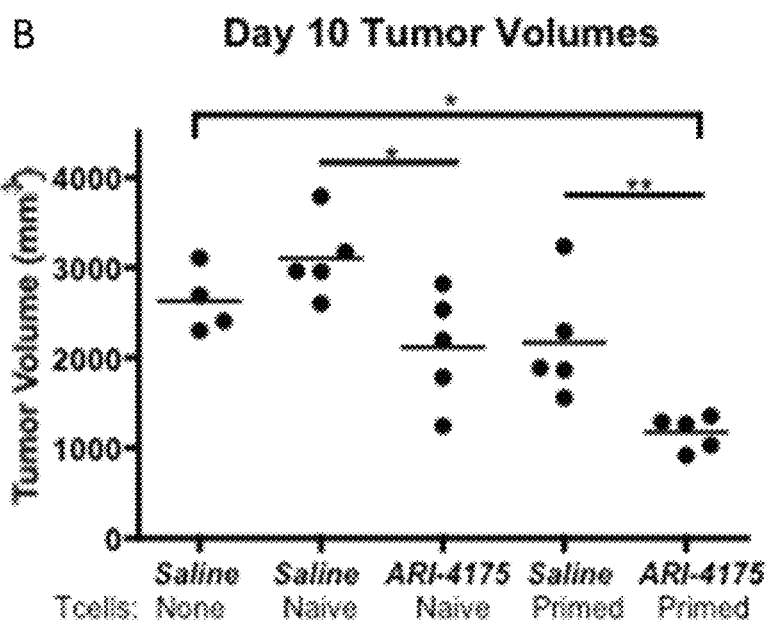

FIGS. 18 A and B show that combination treatment with ARI-4175 and adoptive T cell transfer in Rag1−/− recipients significantly reduces RMS M3-9-M volume. (A) Female Rag1$^{-/-}$ mice received naïve or RMS-primed T cells one day after tumor challenge. (B) By day 10, ARI-4175 treated mice had significantly smaller tumors than saline treated mice (naïve: n=5, p=0.0159; primed: n=5, p=0.0079). Rag1$^{-/-}$ mice treated with tumor-primed T cells in combination with ARI-4175 had the smallest tumors overall.

ARI-4175 is a potent adjuvant to DC vaccination as evidenced by significantly improved survival and reduced RMS M3-9-M volume (FIG. 19). FIG. 19 A shows a late treatment model for DC vaccination and ARI-4175 treatment. FIG. 19 B shows the tumor volume curve (mean±s.d.) and survival curve. Both groups treated with ARI-4175 had significantly improved survival compared to controls (sham vaccine: n=7, p<0.001, DC vaccine: n=7, p<0.001). Mice treated with a combination therapy using ARI-4175 and DC vaccine had significantly smaller tumors compared to mice treated with ARI-4175 alone (n=7, p=0.0481).

The RMS cell line was derived from Ink4a/Arf$^{-/-}$ mice transgenic for hepatocyte growth factor/scatter factor (HGF/SF) that develop malignant RMS with high penetrance. DC vaccine will be prepared by incubating bone marrow derived DCs with apoptotic bodies generated from RMS cells as previously described. Tumor growth was monitored by caliper measurement every 2 days.

Example 3

Induction of IL-1β and Upregulation of Cytokine and Chemokine Expression in Tumors and Draining Lymph Nodes by Ala-boroPro (2243), Val-boroPro (PT-100, 2054), and t-BuGly-boroPro (ARI-4175)

Figure 4:
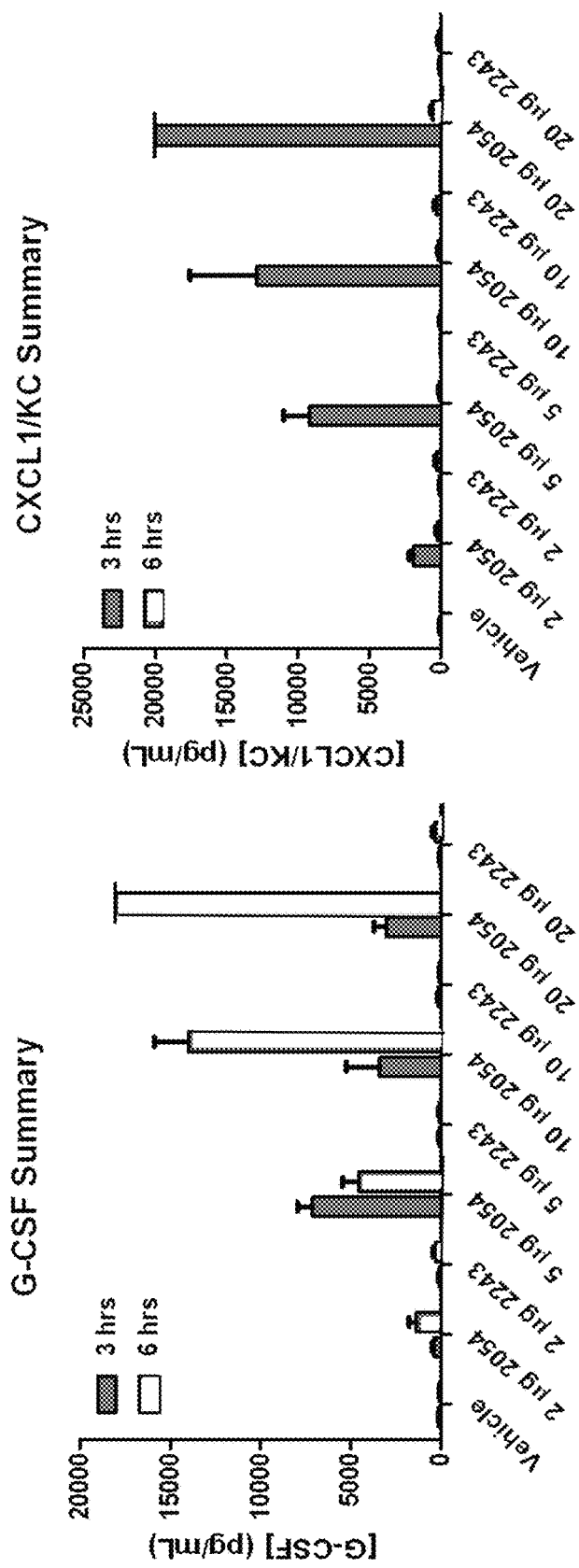
FIG. 4 shows that Val-boroPro (2054 in the figure), but not Ala-boroPro (2054 in the figure), stimulates G-CSF and CXCL1/KC in BALB/c mice. G-CSF and CXL1/KC are markers of anti-cancer immune enhancing activity. The experimental setup and results are discussed in Example 3.
Figure 5:
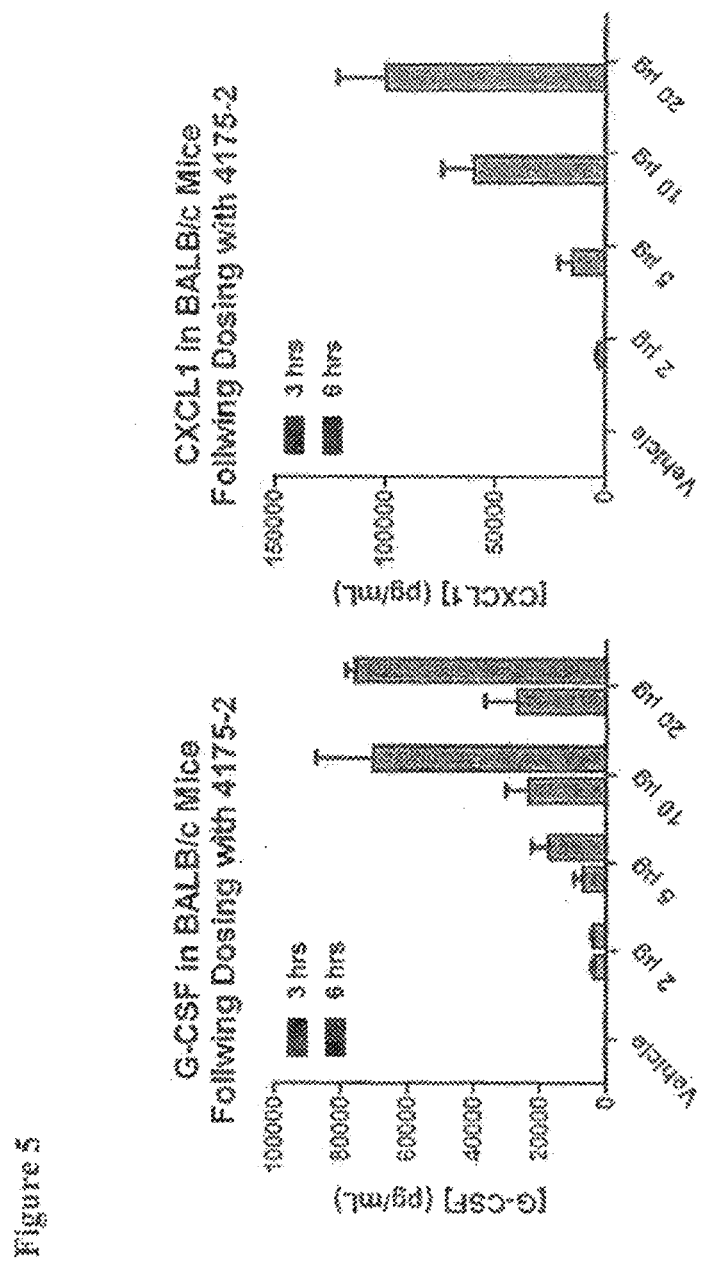
FIG. 5 shows that Ari-4175 (4175-2 in the figure) is a very potent inducer of cytokines in vivo. The experimental setup and results are discussed in Example 3.
Figure 6:
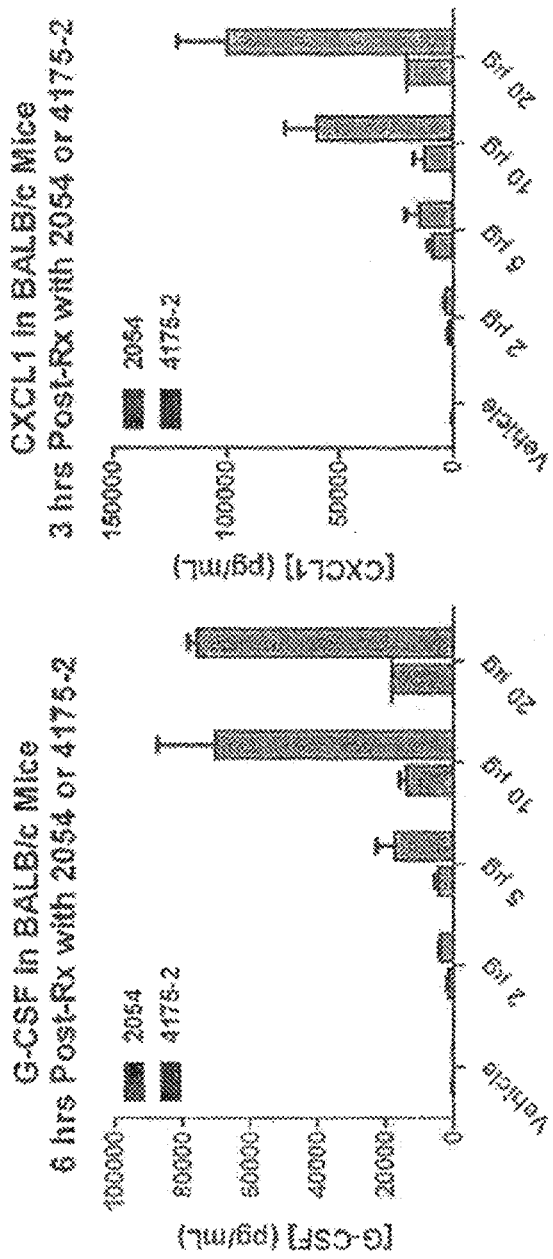
FIG. 6 shows that ARI-4175 (4175-2) is much more potent than PT-100 (2054) at inducing G-CSF and CXCL1 cytokines, which are markers of anti-cancer immune-enhancing activity. The experimental setup and results are discussed in Example 3.

Method for Cytokine Assay in BALB/c Mice. Female BALB/c mice were treated with various doses of PT-100 or ARI-4175 by oral gavage (PO) or intraperitoneal (IP) injection and serum was analyzed for chemokines (FIGS. 4, 5, and 6). Blood was collected by cardiac puncture at various times post-dose and serum was prepared for analysis by ELISA. The samples were assayed for mouse mouse cytokines G-CSF and mouse CXCL1 using ELISA kits from R&D Systems (Cat. No. MCS00 and MKC00B respectively). All measurements were made in duplicate. Serum samples were diluted as necessary to obtain values within the range of the assays. Optimal dilutions required varied depending on the test agent and can range from no dilution for control samples or test agents with no activity to 1:1000 dilution for very high samples. For agents that produce a positive response the strongest signal was observed at 2 hrs post-dose for CXCL1 and at 6 hours post-dose for G-CSF. The dose response varies with test agent but 20 μg/mouse dose is an acceptable baseline dose for response assessment. Typically 6 animals are measured for each agent at each time point.

FIG. 4 demonstrates that Val-boroPro (2054), but not Ala-boroPro (2243), stimulates G-CSF and CXCL1/KC in BALB/c mice. G-CSF and CXL1/KC are markers of anticancer immune enhancing activity.

ARI-4175 (4175-2 in FIGS. 5 and 6) is a very potent inducer of cytokines. Stimulation of G-CSF increased until 6 h after administration; CXCL1 was rapidly induced at 3 h after administration but had disappeared by 6 h (FIG. 5). ARI-4175 (4175-2) is at least 5 times more potent than PT-100 (2054) at inducing G-CSF and CXCL1 cytokines (FIG. 6). Serum from ARI-4175 treated mice also had increased IL-18, IL-1β and IFN-γ compared to vehicle but at much lower levels than G-CSF and CXCL1.

PT-100 stimulates expression of proinflammatory cytokine and chemokine mRNA 2 hours after oral administration to tumor-bearing mice. The PT-100 response is characterized by upregulation of IL-1β, G-CSF, IL-6, CXCL1, CXCL9 and CXCL10 in tumor and lymph node tissue. ARI-4175 was recently found to stimulate development of IL-17 producing T$_h$17 cells in vitro (V. Kuchroo, unpublished data). T$_h$-17 cells appear to contribute to effective antitumor immunity in certain cancers; therefore, IL-17 will be included with the cytokine/chemokine panel characterizing the response to PT-100 that we will investigate after administration of ARI-4175 and PT-100 to RMS-DC vaccinated mice. RNA expression will be assayed in RMS tumor and draining lymph node tissues 2 hours after compound administration at optimal doses. We will use the RT-PCR procedure used previously to analyze the upregulation of cytokines and chemokines by PT-100 in mice bearing A549 lung carcinoma xenografts. cDNA will be synthesized with an iScript kit (Biorad, Hercules, Calif.) from total RNA extracted by Trizol (Invitrogen, Carlsbad, Calif.), diluted 1:10 in water, and amplified for 40 cycles in a thermal cycler (cDNA denaturing, 95° C./15 s; annealing and extension, 60° C./30 s) using 10-μM unlabeled primer pairs in a 2× iQ Sybergreen Supermix (Biorad). Reactions will use Taqman probes 5'-labeled with HEX, FAM or Texas Red and 3'-labeled with black hole quenchers (Biosearch Technologies, Novato, Calif.). Cytokine/chemokine target mRNA and 18s RNA reference control forward/reverse primer pairs and Taqman probes will be designed using Beacon Designer software (Premier Biosoft International, Palo Alto, Calif.). mRNA copy numbers will be calculated from cycle threshold values using standard curves with size-characterized reference cDNA, which will be synthesized and amplified from mouse tissue RNA, purified by electrophoresis and a gel purification kit (Qiagen, Valencia, Calif.), and quantified by PicoGreen (Invitrogen, Carlsbad, Calif.).

Figure 11:
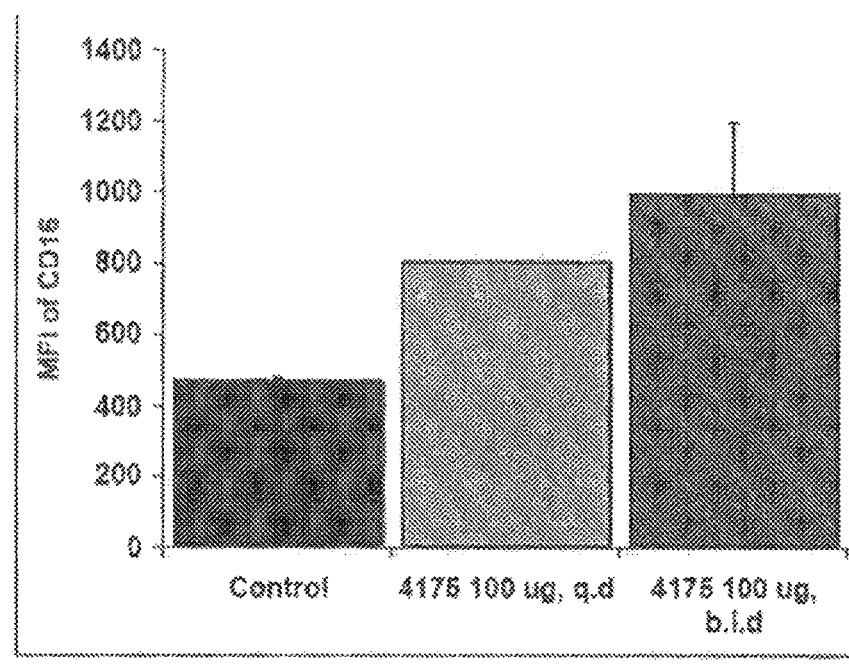
FIG. 11 shows that CD16 expression is upregulated on NK cells taken from nude mice treated with ARI-4175.
Figure 12:
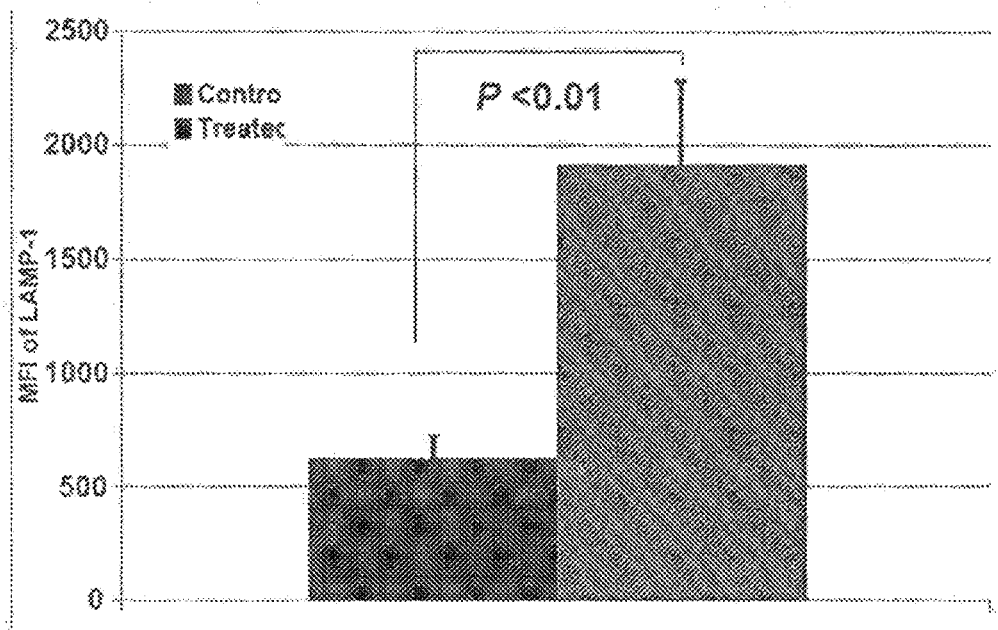
FIG. 12 shows that LAMP-1 (CD107) expression is upregulated on NK cells taken from nude mice treated with ARI-4175.
Figure 15:
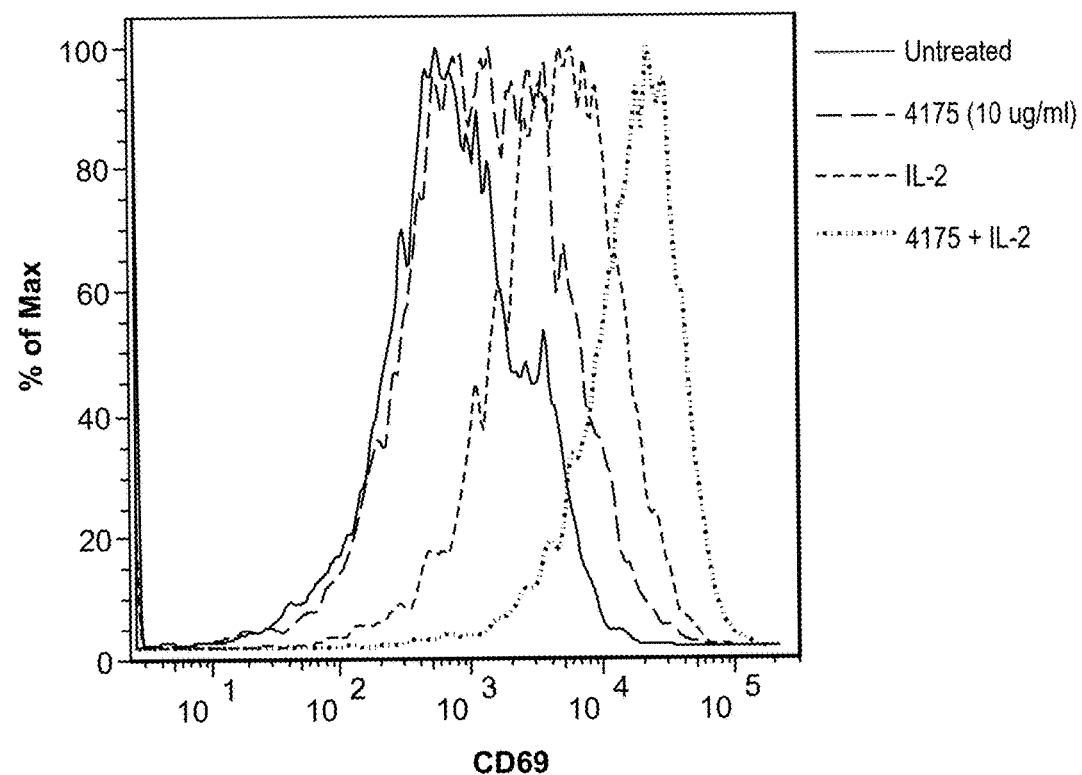
FIG. 15 shows that ARI-4175 induces CD69 on human NK cells. The results shown are with cultured human PBLs from two healthy donors after a 1 day incubation.
Figure 15:
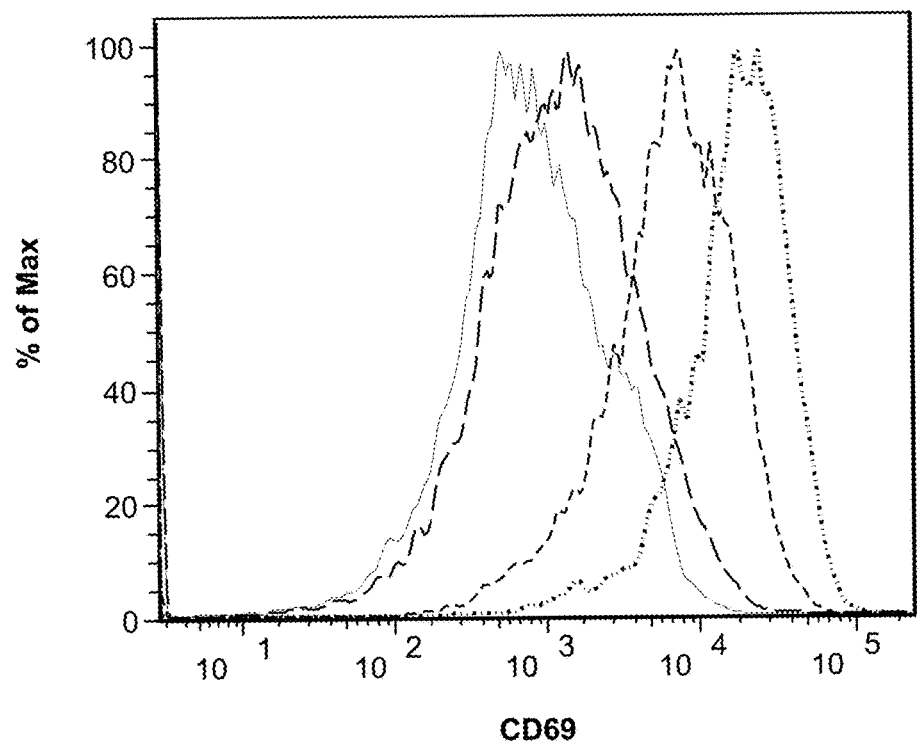

As shown in FIGS. 11 and 12, treatment of mice with ARI-4175 also increased NK cell expression of the FcγRIII receptor, CD16 and the degranulation marker LAMP-1. In vitro treatment of human NK cells also increased the activation marker, CD69 (FIG. 15). The therapeutic effect of ARI-4175 might partially be due to the augmentation of ADCC through elevating expression of CD16 (FcγRIIIA) and activating NK cells (based on CD69 upregulation).

Example 4

Immunological Memory by Tumor Rechallenge of Vaccinated Mice in which Tumor Regression and Rejection Occurs An effective vaccine for cancer would have the advantage of establishing immunological memory that can protect against disseminated metastasis or tumor regrowth following clinical response to initial treatment. Mice in which intramuscular RMS tumors are rejected after RMS DC vaccination followed by ARI-4175 or PT-100 treatment in Example 1 were rechallenged by intramuscular injection of 10×10$^6$ RMS cells at least 20-30 days after rejection of primary tumors. Mice were monitored for secondary tumor growth for a further 20-30 days without any additional therapeutic treatment. In order to demonstrate immunological specificity of protection, mice will also be challenged with the C57BL/6 tumor cell line, EL4 (ATCC, TIB-39). Groups of 4 mice were tested for immunological memory. Similar experiments demonstrating tumor-specific memory following PT-100 treatment have been described.

Figure 7:
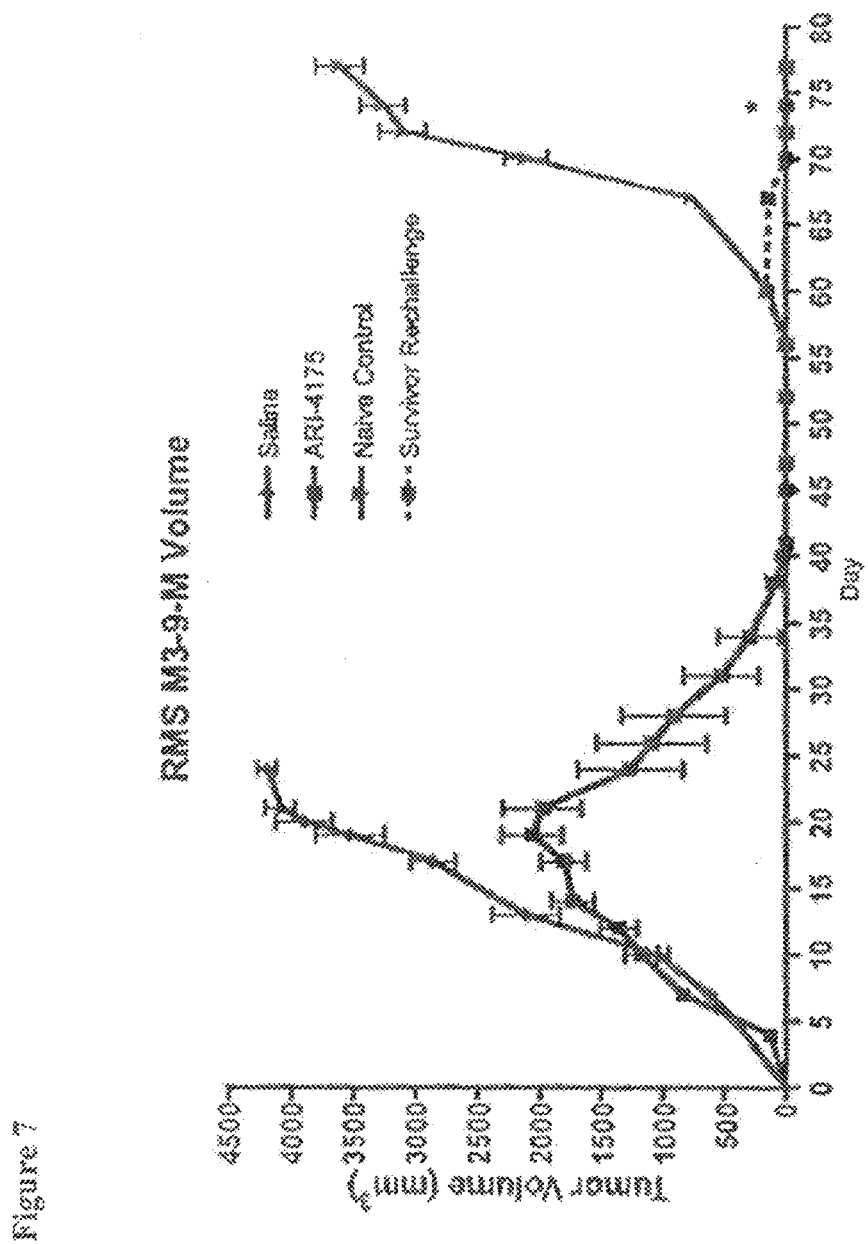
FIG. 7 shows that ARI-4175 establishes immunity to tumor rechallenge in the M3-9-M RMS model. The experimental setup and results are discussed in Example 4.

As shown in FIG. 7, female C57BL/6 mice were challenged intramuscularly with $1\times10^6$ RMS M3-9-M on day 0. Mice were orally gavaged with 200 µg ARI-4175 on days 3-7, 17-21, 24-28, and 31-35. Tumor-free survivors were rechallenged on day 56 with $5\times10^5$ RMS M3-9-M and monitored with no additional 4175 treatment. Following rechallenge, RMS M3-9-M showed initial growth followed by rejection in all mice (n=7, p=0.0175).

Example 5

Assay Tumor-Specific CTL in RMS DC Vaccinated Mice

CTL will be assayed ex vivo by the $^{51}$Cr-release assay in tumor-draining lymph nodes and spleens of RMS tumor-bearing mice receiving the RMS DC vaccine and ARI-4175 or PT-100 treatments described in Example 1. The assay will be performed as previously described for the measurement of tumor-specific CTL responses stimulated by PT-100 in EL4 tumor-inoculated C57BL/6 mice. Specificity of CTLs will be investigated by comparing cytotoxicity against RMS versus EL4 cells.

Example 6

MTDs of ARI-4175 and PT-100 in C57BL/6 Mice

Previously, in C57BL/6 mice administered PT-100 at doses above the MTD (~2 mg/kg/day), no obvious signs of toxicity were observed prior to death; therefore, the end point for determination of MTD was mortality in this experiment. In order to gain insight into the causes of toxicity, histopathology was investigated to determine the dose response of plasma cytokine and chemokine levels. The cytokine/chemokine assay was used to determine whether toxicity is related to PT-100's putative mechanism of action. Preliminary experiments indicated that blockade of cytokine/chemokine responses with the IL-1R antagonist, anakinra, does not alter the toxicity of PT-100 in rats, suggesting that the toxicity of PT-100 may not be due to systemic cytokine/chemokine production.

Summary of Rat Toxicity. A maximum tolerated dose (MTD) study was undertaken to compare the MTD for ARI-4175 (t-BuGly-boroPro) and PT-100 (Val-boroPro, ARI-2054) in Sprague Dawley rats. Animals were dosed by either subcutaneous injection (SQ) or oral gavage (PO). Six animals were used at each dose. A blood sample was drawn from the tail at 30 minutes post-dose which was used to measure plasma drug concentrations. The starting dose for both compounds was 0.05 mg/kg body weight and then the dose was adjusted up or down for each drug to determine the maximum dose at which there was 100% survival. At the starting dose of 0.05 mg/kg body weight SQ, both ARI-4175 and PT-100 treatment resulted in at least one animal death within the first 24 hours. A 0.01 mg/kg body weight dose, SQ, did not result in any deaths and no adverse effects were observed for 48 hours post-dose. A third experiment was done at a dose of 0.025 mg/kg body weight which resulted in one death in the ARI-4175 group but no deaths in the PT-100 group. The study was repeated with oral dosing starting again at 0.05 mg/kg body weight. Both drugs were apparently more tolerated by the oral dose as there were no adverse effects in this experiment at 0.05 mg/kg PO. Increasing the dose to 0.1 mg/kg PO resulted in 2 deaths in the PT-100 group but no adverse effects with ARI-4175. At 0.25 mg/kg ARI-4175 PO there was one death. Therefore the MTD observed for SQ was 0.025 mg/kg for PT-100 and 0.01 mg/kg for ARI-4175. By the oral route the MTD was 0.05 mg/kg for PT-100 and 0.1 mg/kg for ARI-4175. Evaluation of the plasma drug concentrations suggests toxicity results at equivalent plasma drug concentrations regardless of the route of administration. Toxicity is observed for the dose of drug that results in plasma drug concentration of 100+/−50 nM. This data is summarized in FIG. 20.

Mouse Toxicity Plasma Vs. Dose Figures. C57BL/6 mice were treated by oral gavage at various doses up to 40 mg/kg of ARI-4175 and up to 10 mg/kg of PT-100 (ARI-2054) daily for 5 days. On the $5^{th}$ day blood was drawn pre-dose and at 30 minutes post-dose and plasma drug concentrations were measured by LCMS. Oral availability of PT-100 is 3-4 times greater than that of ARI-4175 as evidenced by the plasma concentrations at the 10 mg/kg dose. Plasma concentrations are approximately proportional to dose over the range tested. Survival was 100% in this experiment but all groups showed significant weight loss over the 5 day treatment period. The results are shown in FIG. 21.

PK for 4175 in Mice. Pharmacokinetics of ARI-4175 was measured in normal BALB/c mice in both the open (linear) and closed (cyclic) forms of the drug by oral gavage (PO) and by, intraperitoneal (IP), subcutaneous (SQ) and intravenous (IV) injection. The open form of the drug was prepared by incubation of the drug at room temperature overnight at pH 2. The closed form was prepared by incubation overnight at pH 7.4 (in PBS). The open (linear) samples were neutralized by dilution into PBS immediately before administration. The treatment groups are listed below (Table 2).

Blood

TABLE 2

| Group | Dose | Route | n |
|---|---|---|---|
| 1 | 1 mpk | PO | 4 |
| 2 | 1 mpk | IP | 4 |
| 3 | 1 mpk | SQ | 4 |
| 4 | 0.5 mpk | IV | 6 | was collected from the tail vein for all groups except the IV groups. The IV injection was made in the tail vein and therefore blood was collected from a distant site (submandibular vein). Plasma samples were prepared and the concentration of ARI-4175 in each sample was measured by LC-MS. The results are shown in FIG. 22.

Example 7

Investigation of Histopathology in Mice Receiving Escalating Doses of ARI-4175 and PT-100

Groups of 3 mice will be inoculated intramuscularly with RMS cells and administered PT-100 and ARI-4175 by gavage at doses increasing from the MED determined in Example 1 up to the MTD determined in Example 6. One 5-day cycle of each compound will be given from day 10 to day 14 after tumor inoculation, and on day 18, specimens of tumor, draining lymph node, spleen, liver, lung and kidney tissue will be fixed in formalin and embedded in paraffin. H&E stained tissue sections from test mice will be compared histologically with sections from control mice. PT-100 has been shown to stimulate leukocytic infiltration of solid tumors. The tumor infiltrates are characterized by neutrophils concentrated at the borders of tumor and stromal tissue. Comparison of tumor sections from ARI-4175 treated mice versus sections from PT-100 treated mice will determine whether ARI-4175 also promotes tumor infiltration. It is possible that the toxicity of PT-100 results from leukocytic infiltration of non-tumor tissues leading to inflammatory responses that cause organ failure. Therefore, we will examine the non-tumor tissue samples for the presence of leukocytes in mice treated with PT-100 and ARI-4175.

Example 8

Investigation of Role of Systemic Cytokines/Chemokines in Toxicity Using IL-1 Receptor Deficient Mice Cytokine/chemokine responses to PT-100 are abrogated in IL-1R1 deficient B6.12957-Il1r1$^{tm1Imx}$/J mice (Jackson Laboratory); therefore, if toxicity is due to activity of systemic cytokines/chemokines, MTD should be significantly increased in IL-R1 mutant mice relative to congenic C57BL/6 mice. Therefore, the dose responses of serum G-CSF and CXCL1 cytokines will be compared by ELISA (R&D Systems) and the MTDs of ARI-4175 and PT-100 in B6.129S7-Il1r1$^{tm1Imx}$/J versus C57BL/6 control mice. MTDs will be determined in groups of 3 mice treated at increasing dose levels. G-CSF and CXCL-1 levels will be determined in serum sampled at 3 and 8 hours after compound administration. If IL-1R1 deficient mice are resistance to toxicity, and if histopathology in Experiment 6 reveals leukocytic infiltration of non-tumor tissue, IL-1R1 deficient and sufficient mice will be compared histologically to determine if toxicity is related to inflammatory disruption of organ function.

Example 9

Potential Anti-tumor and Immunologic Effects of ARI-4175 in KRAS Mutated Colorectal Cancer Cell Lines; Co-Administration of ARI-4175 with Cetuximab Cetuximab (CTX) is an effective therapeutic agent in a number of malignancies. Current data indicate that about 40% of colorectal cancer patients bearing mutated K-ras do not benefit from this agent. A possible mechanism of the antitumor effect of cetuximab is mediated through antibody-dependent cell-mediated cytotoxicity (ADCC). This study investigated the potential of activity of ARI-4175, in the treatment of K-ras mutant colorectal cancer xenografts as a single agent or in combination with cetuximab.

Figure 10:
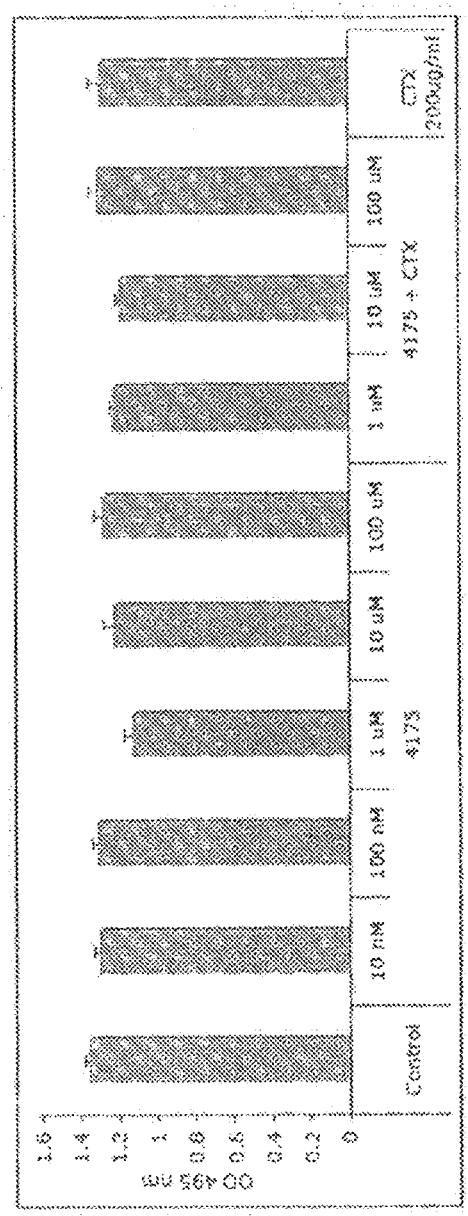
FIG. 10 shows that ARI-4175 (4175) does not exhibit significant in vitro activity against colorectal cancer cell lines. There is also no activity when 4175 is combined with cetuximab (CTX). This is expected, since the antitumor effects of ARI-4175 and cetuximab are thought to be mediated through antibody-dependent cell-mediated cytotoxicity (ADCC).
Figure 13A:
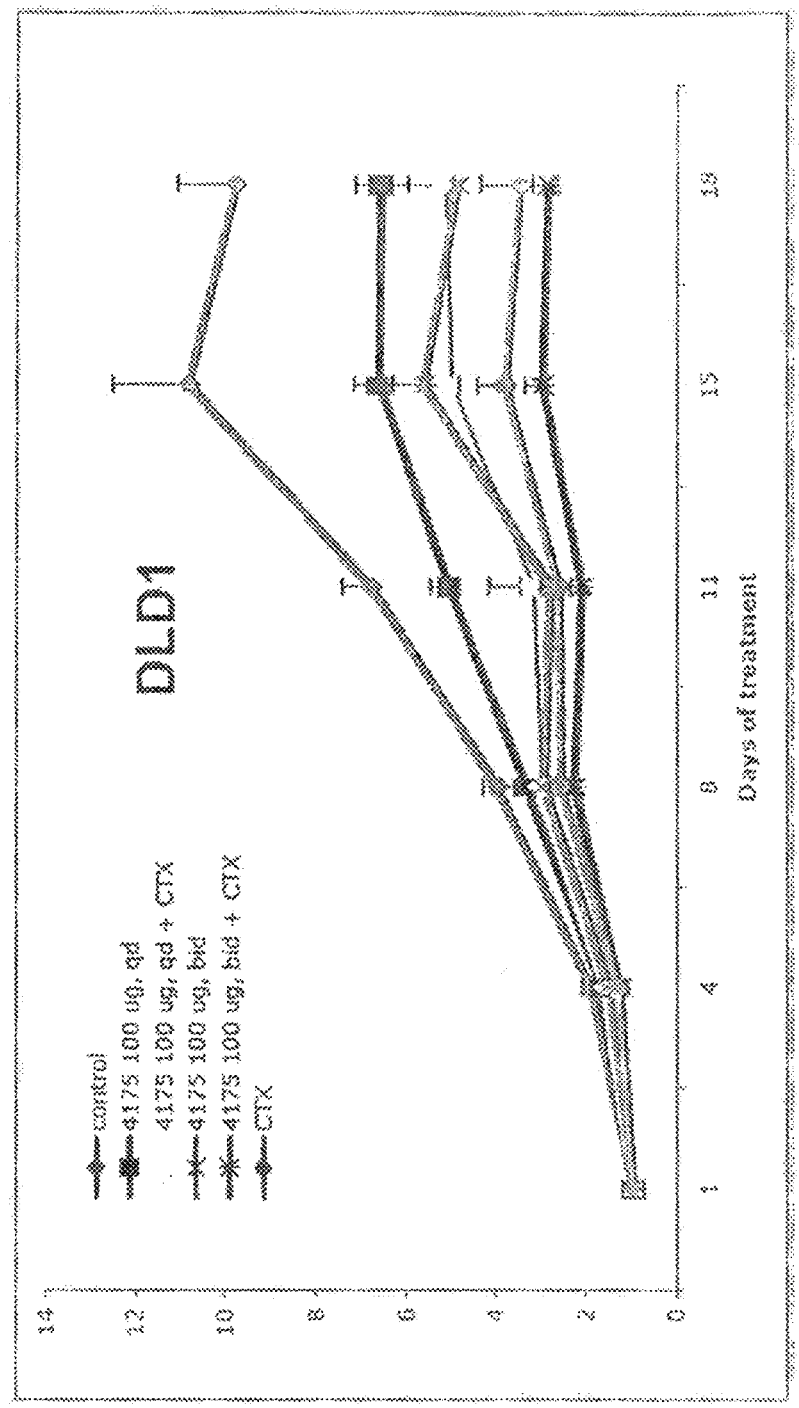
FIG. 13 A shows the in vivo inhibition by ARI-4175 of colon cancer xenografts. The figure shows the inhibition of DLD1 xenografts by ARI-4175 alone or in combination with cetuximab (CTX).
Figure 13:
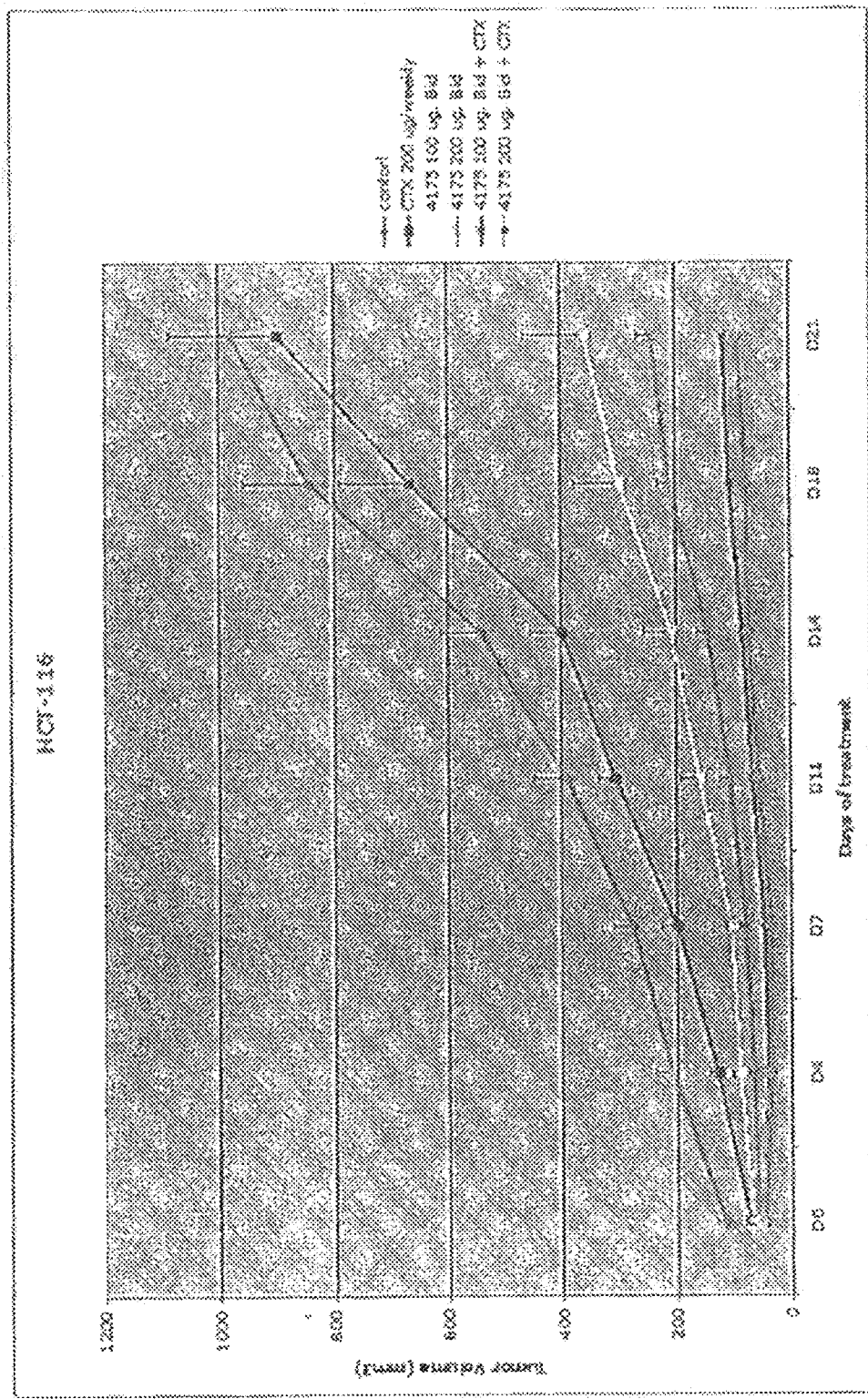
Figure 14:
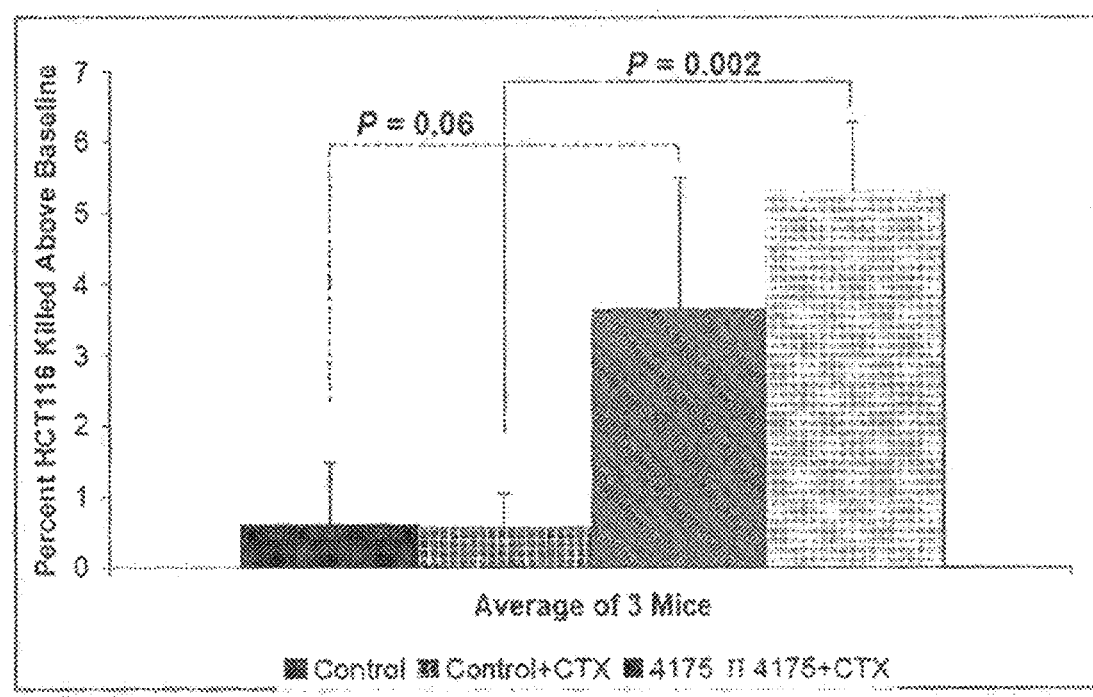
FIG. 14 shows that cytotoxicity of splenocytes from C57Bl/6 non-tumor-bearing mice treated with ARI-4175 and/or cetuximab (CTX) is enhanced against HCT116 tumor cells.

The effect of ARI-4175 alone or in combination with cetuximab was evaluated both in vitro and in vivo. In vitro, the proliferation of K-ras mutant colon cancer cell lines DLD-1 and HCT-116 was detected after three days of culture in the medium containing various concentrations of ARI-4175 or cetuximab (FIG. 10). ARI-4175 (10 nM-200 μM) alone or in combination with cetuximab did not show significant cytotoxicity on either DLD-1 or HCT-116 in cell culture (FIG. 10). In vivo, nude mice bearing DLD-1 or HCT-116 xenograft tumors were randomly divided into four groups, control, ARI-4175 alone, cetuximab alone and ARI-4175 plus cetuximab. ARI-4175 was administered orally at 100 μg, q.d or b.i.d and cetuximab was injected intraperitoneally at 200 μg per week. Tumor measurements were conducted twice a week. In mice growth of both DLD-1 and HCT-116 tumors were significantly blocked by the application of ARI-4175 in a dose-dependent manner (FIGS. 13 A and B). The combination of ARI-4175 with cetuximab led to a further decrease in tumor size although not statistically significant, probably due to lower number of animals. Cetuximab alone did not show any therapeutic effect on HCT-116 xenograft but did have moderate efficacy on DLD-1 tumors.

Example 10

Figure 16:
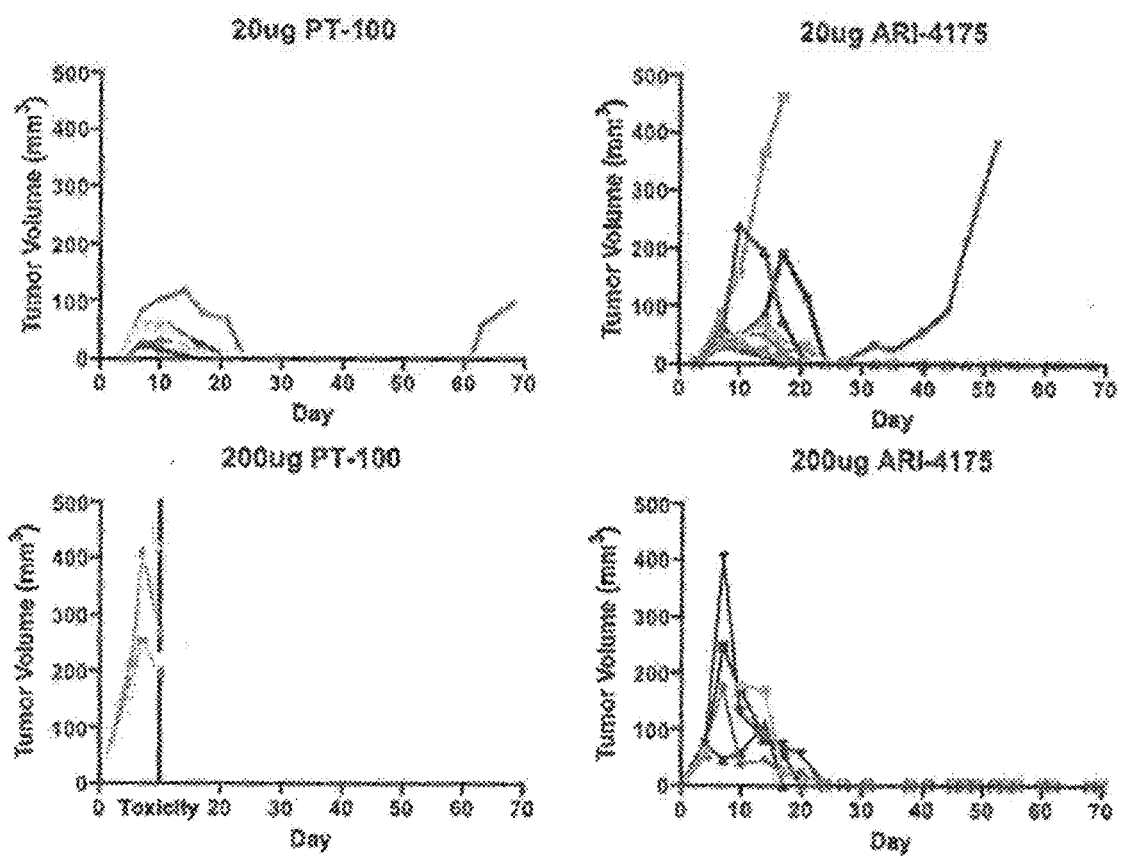
FIG. 16 shows that ARI-4175 is as effective as PT-100 but less toxic at a high dose.

Comparison of Pharmacokinetic Profile of PT-100 and ARI-4175, Other Differences Between the Two Compounds As shown in FIG. 16, female C57BL/6 mice were challenged subcutaneously with 1×10$^6$ MB49. Mice were orally gavaged on days 3-7 and 10-14. Tumor volume was monitored by caliper measurements. At a 20 μg dose, both PT-100 and ARI-4175 induce anti-tumor activity. ARI-4175 dosing at 200 μg induced full regression in 5 of 5 mice whereas PT-100 was toxic at the same dose.

Despite the small differences in chemical structure between PT-100 and ARI-4175, there are unexpectedly large differences in the pharmacokinetic (PK) profile of the two compounds. In particular, the toxicity of ARI-4175 is much lower.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method for enhancing T-cell immunity against tumor cells, comprising:
administering to a patient having a tumor a therapeutically effective amount of a DASH inhibitor to (i) enhance T-cell immunity against the tumor, and (ii) increase serum levels of G-CSF and CXCL1 cytokines,
wherein:
(a) at the therapeutically effective amount the DASH inhibitor is characterized by a pharmacokinetic profile of being an inhibitor of DPP8, DPP9, and DPP4;
(b) the therapeutically effective amount of the DASH inhibitor produces full tumor regression in the patient;
(c) the therapeutically effective amount of the DASH inhibitor is less than the maximum tolerated dose for the patient; and
(d) the DASH inhibitor is represented by Formula I:

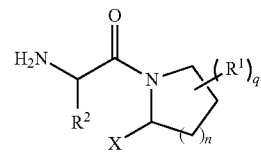

Formula I wherein:

X is B(Y$^1$)(Y$^2$) or CN;

Y$^1$ and Y$^2$ are independently OH, or together with the boron atom to which they are attached represent a group that is hydrolysable to a boronic acid, or together with the boron atom to which they are attached form a 5- to 8-membered ring that is hydrolysable to a boronic acid;

R$^1$ is selected from the group consisting of halogen, lower alkyl, lower alkenyl, lower alkynyl, carbonyl, carboxyl, ester, formate, ketone, thiocarbonyl, thioester, thioacetate, thioformate, amino, acylamino, amido, nitro, sulfate, sulfonate, sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$, azido, cyano, isocyanato, thiocyanato, isothiocyanato, cyanato, $$-N{\overset{\oplus}{\equiv}}{\overset{\ominus}{C}}, \text{ and } -C{\equiv}C-R_8;$$

R$_7$ represents a substituted or unsubstituted aryl, aralkyl, cycloalkyl, cycloalkenyl, or heterocycle;

R$_8$ independently represents hydrogen, —CH$_3$, or —(CH$_2$)$_n$—CH$_3$;

m is 0, 1, 2, 3, 4, 5, or 6;

R$^2$ is a hydrophobic group selected from the group consisting of n-propyl, C$_4$-C$_8$ alkyl, C$_2$-C$_8$alkenyl, C$_2$-C$_8$alkynyl, C$_3$-C$_8$cycloalkyl, C$_2$-C$_7$heterocyclyl, aryl, heteroaryl, aralkyl, heteroaralkyl, and side chains of naturally occurring hydrophobic amino acids;

n is 0, 1,or 2; and q is 0, 1, 2, 3, or 4.

2. The method of claim 1, wherein:
the maximum tolerated dose of the DASH inhibitor in C57BL/6 mice is at least 10 mg/kg;
and the DASH inhibitor induces full tumor regression in C57BL/6 mice at a dose less than the maximum tolerated dose in C57BL/6 mice.

3. The method of claim 1, wherein the DASH inhibitor is administered as part of a cancer vaccine therapy.

4. The method of claim 3, wherein the cancer vaccine therapy is a dendritic cell vaccine therapy.

5. The method of claim 1, wherein the DASH inhibitor enhances antibody-dependent cell-mediated cytotoxicity of an antibody treatment.

6. The method of claim 5, wherein the antibody treatment is selected from the group consisting of trastuzumab, cetuximab, bevacizumab, and rituximab.

7. The method of claim 1, wherein the DASH inhibitor is administered with one or more chemotherapeutic agents.

8. The method of claim 7, wherein the one or more chemotherapeutic agents are selected from the group consisting of ipilimumab, vemurafenib, GDC-0879, PLX-4720, aldesleukin, asparaginase, bleomycin sulfate, carboplatin, chlorambucil, cisplatin, cladribine, cyclophosphamide, cytarabine, dacarbazine, dactinomycin, daunorubicin hydrochloride, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-α2a, interferon-α2b, interferon-αn3, interferon-α1b, interleukins, irinotecan, mechlorethamine hydrochloride, melphalan, mercaptopurine, methotrexate, methotrexate sodium, mitomycin, mitoxantrone, paclitaxel, pegaspargase, pentostatin, prednisone, profimer sodium, procarbazine hydrochloride, taxol, taxotere, teniposide, topotecan hydrochloride, vinblastine sulfate, vincristine sulfate, and vinorelbine tartrate.

9. The method of claim 1, wherein the DASH inhibitor enhances T-cell immunity against tumors selected from the group consisting of carcinoma, sarcoma, leukemia, lymphoma, and myeloma.

10. The method of claim 1, wherein the DASH inhibitor enhances T-cell immunity against tumors selected from the group consisting of lung tumors, lymphomas, breast tumors, colorectal tumors, thyroid tumors, uterine tumors, pancreatic tumors, prostate tumors, skin tumors, kidney tumors, liver tumors, and brain tumors.

11. The method of claim 1, wherein the DASH inhibitor induces immunological memory to rechallenge by the tumor cells.

12. The method of claim 1, wherein the patient is a human.

13. The method of claim 1, wherein the DASH inhibitor is administered orally.

14. A method for treating a patient in remission of a tumor to avoid relapse, comprising administering to a patient in remission of a tumor an effective amount of a DASH inhibitor to (i) enhance T-cell immunity against the tumor, and (ii) increase serum levels of G-CSF and CXCL1 cytokines, wherein:

(a) at the therapeutically effective amount the DASH inhibitor is characterized by a pharmacokinetic profile of being an inhibitor of DPP8, DPP9, and DPP4;

(b) the therapeutically effective amount of the DASH inhibitor produces full tumor regression in the patient;

(c) the therapeutically effective amount of the DASH inhibitor is less than the maximum tolerated dose for the patient; and (d) the DASH inhibitor is represented by Formula I:

Formula I wherein:

X is B(Y$^1$)(Y$^2$) or CN;

Y$^1$ and Y$^2$ are independently OH, or together with the boron atom to which they are attached represent a group that is hydrolysable to a boronic acid, or together with the boron atom to which they are attached form a 5- to 8-membered ring that is hydrolysable to a boronic acid;

R$^1$ is selected from the group consisting of halogen, lower alkyl, lower alkenyl, lower alkynyl, carbonyl, carboxyl, ester, formate, ketone, thiocarbonyl, thioester, thioacetate, thioformate, amino, acylamino, amido, nitro, sulfate, sulfonate, sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$ —S-lower alkenyl, —(CH$_2$)$_n$—S—(CH$_2$)$_m$—R$_7$, azido, cyano, isocyanato, thiocyanato, isothiocyanato, cyanato,

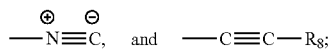

R$_7$ represents a substituted or unsubstituted aryl, aralkyl, cycloalkyl, cycloalkenyl, or heterocycle;

R$_8$ independently represents hydrogen, —CH$_3$, or —(CH$_2$)$_n$—CH$_3$;

m is 0, 1, 2, 3, 4, 5, or 6;

R$^2$ is a hydrophobic group selected from the group consisting of n-propyl, C$_4$-C$_8$ alkyl, C$_2$-C$_8$alkenyl, C$_2$-C$_8$alkynyl, C$_3$-C$_8$cycloalkyl, C$_2$-C$_7$heterocyclyl, aryl, heteroaryl, aralkyl, heteroaralkyl, and side chains of naturally occurring hydrophobic amino acids;

n is 0, 1, or 2; and q is 0, 1, 2, 3, or 4.

15. The method of claim 14, wherein the patient is a human.

16. The method of claim 14, wherein the DASH inhibitor is administered orally.

* * * * *

UNITED STATES PATENT AND TRADEMARK OFFICE
CERTIFICATE OF CORRECTION

PATENT NO. : 9,839,646 B2  
APPLICATION NO. : 14/948777  
DATED : December 12, 2017  
INVENTOR(S) : William W. Bachovchin Page 1 of 1

It is certified that error appears in the above-identified patent and that said Letters Patent is hereby corrected as shown below:

In the Specification

At Column 1, Line 13, insert:
-- GOVERNMENT SUPPORT
This invention was made with government support under grant number CA174031 awarded by the National Institutes of Health. The government has certain rights in the invention. --

Signed and Sealed this
Thirty-first Day of December, 2019

Andrei Iancu
*Director of the United States Patent and Trademark Office*